US012807921B2

(12) United States Patent
Kim et al.

(10) Patent No.: US 12,807,921 B2
(45) Date of Patent: Nov. 24, 2026

(54) METHOD FOR MASS PRODUCTION OF HIGHLY PURE, STEM CELL-DERIVED EXTRACELLULAR VESICLE BY USING PEPTIDE

(71) Applicants: INDUSTRY-ACADEMIC COOPERATION FOUNDATION, CHOSUN UNIVERSITY, Gwangju (KR); KONKUK UNIVERSITY INDUSTRIAL COOPERATION CORP, Seoul (KR)

(72) Inventors: Tae-Hyoung Kim, Gwangju (KR); Jung Hee Park, Gwangju (KR); Ji-Hye Han, Gwangju (KR); Seung-Hyun Myung, Gwangju (KR); Ssang-Goo Cho, Seoul (KR); Kyung Min Lim, Seoul (KR); Yoon Joo Lee, Seoul (KR)

(73) Assignee: STEMEXONE., LTD., Daejeon (KR)

( * ) Notice: Subject to any disclaimer, the term of this patent is extended or adjusted under 35 U.S.C. 154(b) by 654 days.

(21) Appl. No.: 18/267,230

(22) PCT Filed: Dec. 10, 2021

(86) PCT No.: PCT/KR2021/018761

§ 371 (c)(1),
(2) Date: Jun. 14, 2023

(87) PCT Pub. No.: WO2022/131700

PCT Pub. Date: Jun. 23, 2022

(65) Prior Publication Data

US 2024/0043797 A1 Feb. 8, 2024

(30) Foreign Application Priority Data

Dec. 14, 2020 (KR) ........................ 10-2020-0174891

(51) Int. Cl.

*C12N 5/073* (2010.01)
*A23L 33/10* (2016.01)
*A61P 17/02* (2006.01)
*A61P 29/00* (2006.01)

(52) U.S. Cl.

CPC ............ *C12N 5/0605* (2013.01); *A23L 33/10* (2016.08); *A61P 17/02* (2018.01); *A61P 29/00* (2018.01); *C12N 2500/30* (2013.01); *C12N 2500/34* (2013.01); *C12N 2501/734* (2013.01)

(58) Field of Classification Search

None
See application file for complete search history.

(56) References Cited

U.S. PATENT DOCUMENTS

| | | | | |
|---|---|---|---|---|
| 11,248,024 B2 * | 2/2022 | Kim | C07K 14/4747 |
| 12,280,148 B2 * | 4/2025 | Kim | A61K 38/177 |
| 2020/0297761 A1 * | 9/2020 | Ding | A61K 35/12 |
| 2023/0220348 A1 * | 7/2023 | Cho | A61P 3/10 424/1.21 |

FOREIGN PATENT DOCUMENTS

| | | |
|---|---|---|
| KR | 10-2019-0116858 A | 10/2019 |
| KR | 10-2189574 B1 | 12/2020 |

OTHER PUBLICATIONS

"Hypothetical protein DBR06_SOUSAS8910029, partial [Sousa chinensis]," GenBank Accession No. TEA35552.1, NCBI. (Mar. 22, 2019) (1 page).
Da Silva Novaes et al., "Influence of high glucose on mesangial cell-derived exosome composition, secretion and cell communication," Sci. Rep. 9(1):6270 (Apr. 2019) (13 pages).
International Search Report and Written Opinion mailed Mar. 22, 2022, for PCT International Application No. PCT/2021/018761, Kim et al., "Method for Mass Production of Highly Pure, Stem Cell-Derived Extracellular Vesicle by Using Peptide," filed Dec. 10, 2021 (partial English translation) (10 pages).
Martinez-Lópe z et al., "Small extracellular vesicles secreted by Candida albicans hyphae have highly diverse protein cargoes that include virulence factors and stimulate macrophages," bioRxiv preprint (Oct. 5, 2020) (51 pages).

* cited by examiner

*Primary Examiner* — Nghi V Nguyen
(74) *Attorney, Agent, or Firm* — Clark+Elbing LLP

(57) ABSTRACT

The present disclosure relates to a method for mass production of extracellular vesicles by using a noxa protein-derived peptide and mesenchymal stem cells and, more specifically, to a method for mass production of extracellular vesicles having wound healing and immunomodulatory effects, wherein mesenchymal stem cells are cultured in a medium composition containing a noxa protein-derived peptide, glucose, sucrose, and 3-(N-morpholino)propanesulfonic acid [MOPS], whereby the extracellular vesicles can be obtained at high yield with high purity.

8 Claims, 24 Drawing Sheets

Specification includes a Sequence Listing.

【Fig. 1】
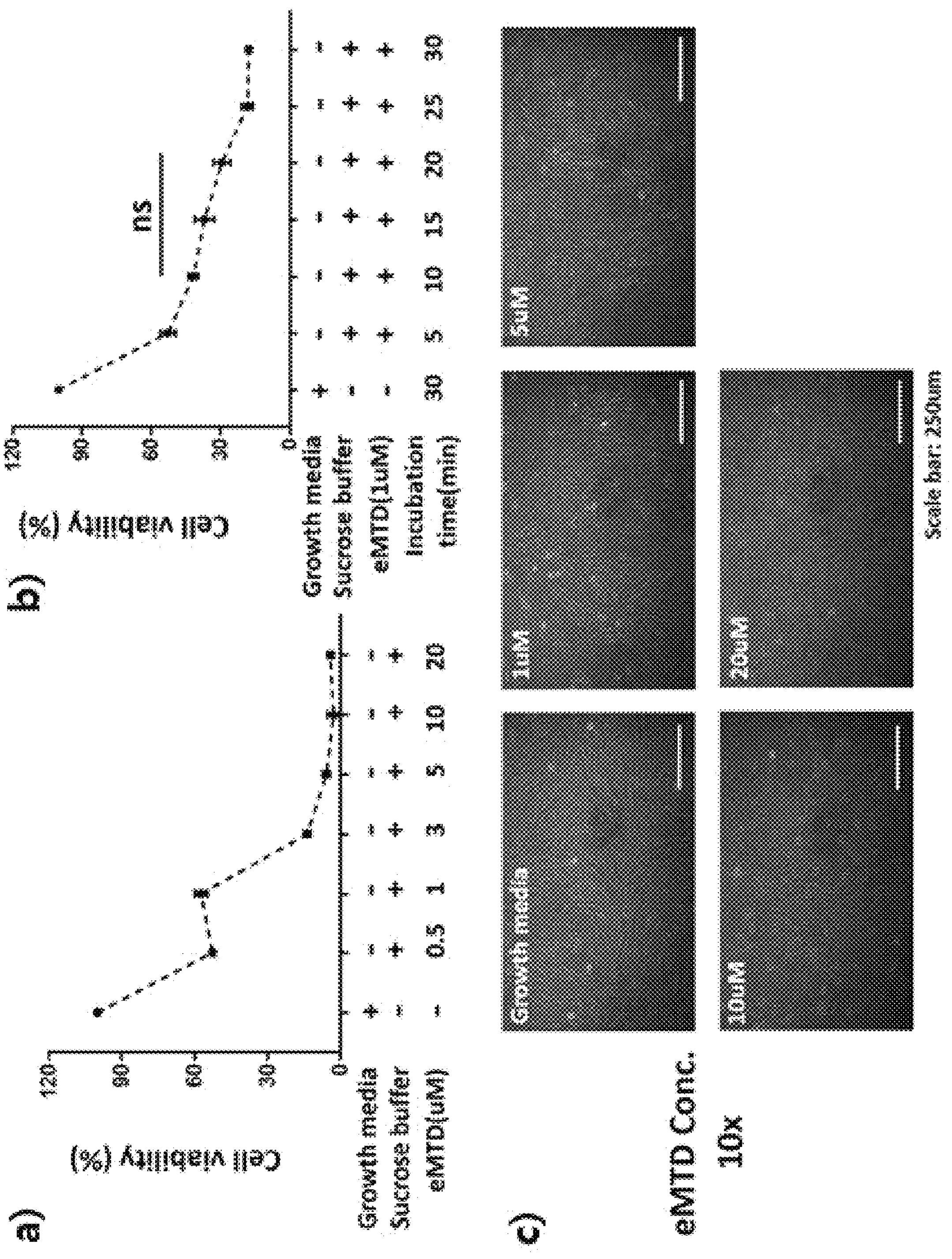

[Fig. 2]
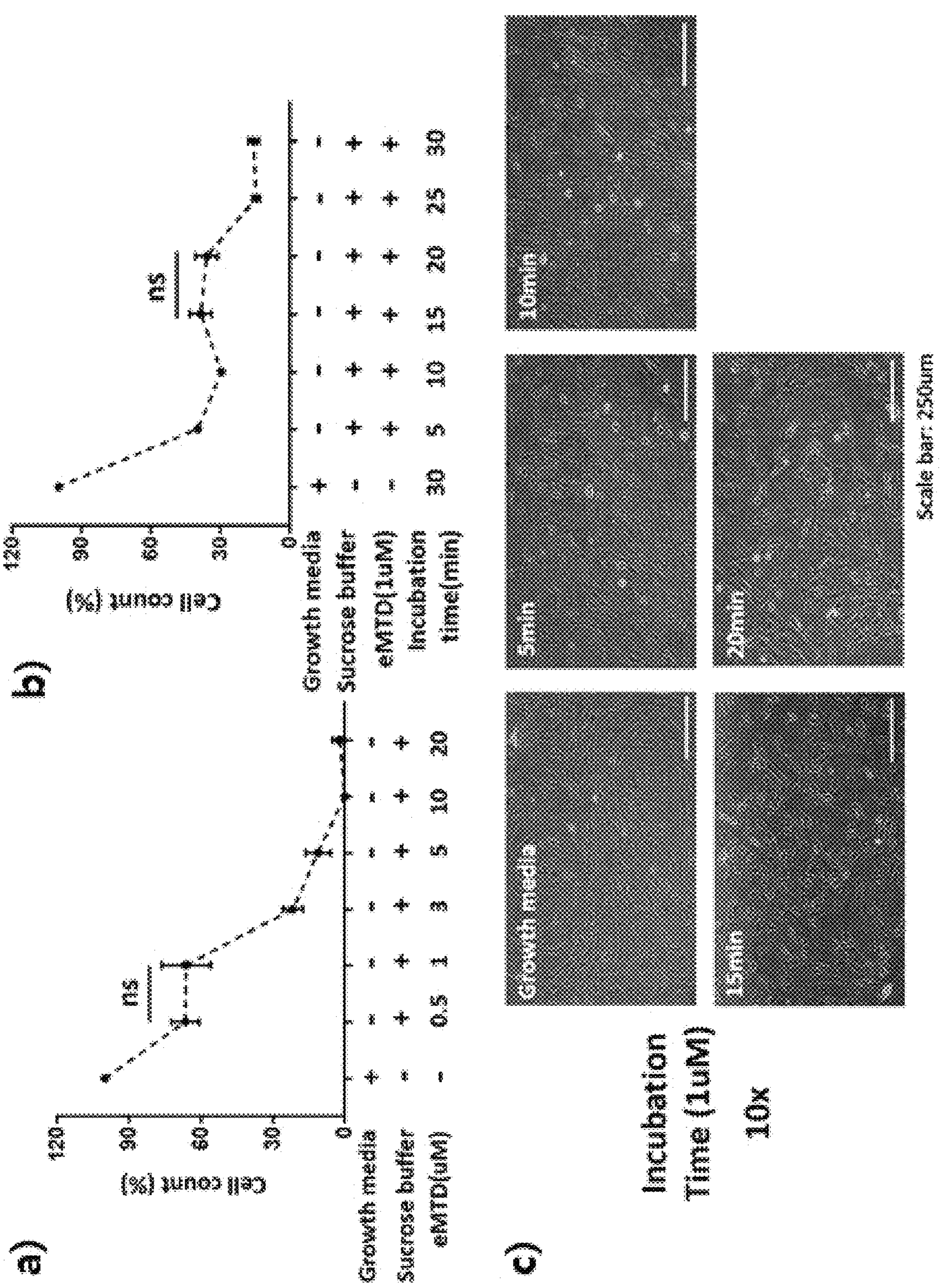

【Fig. 3】
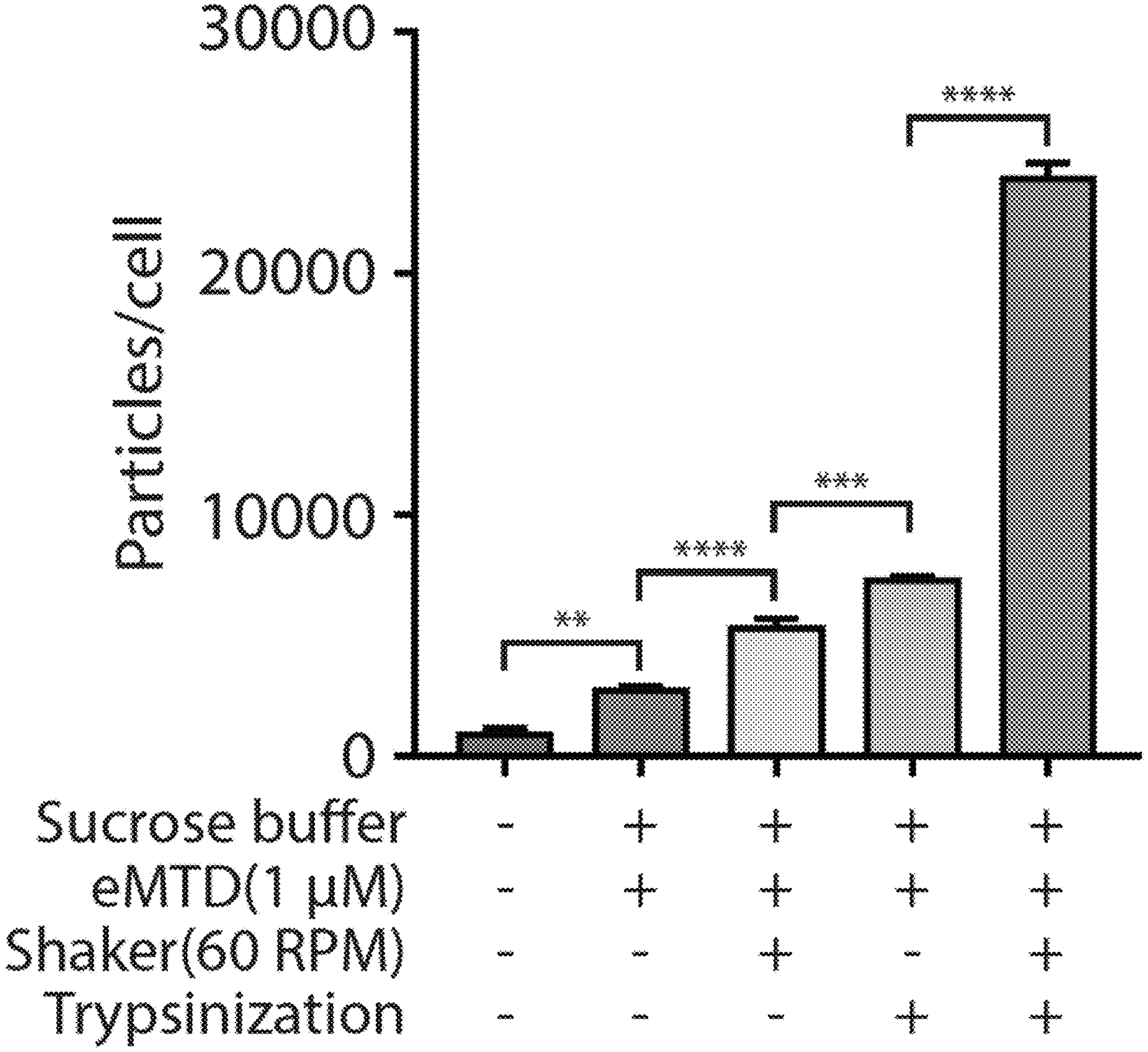

【Fig. 4a】
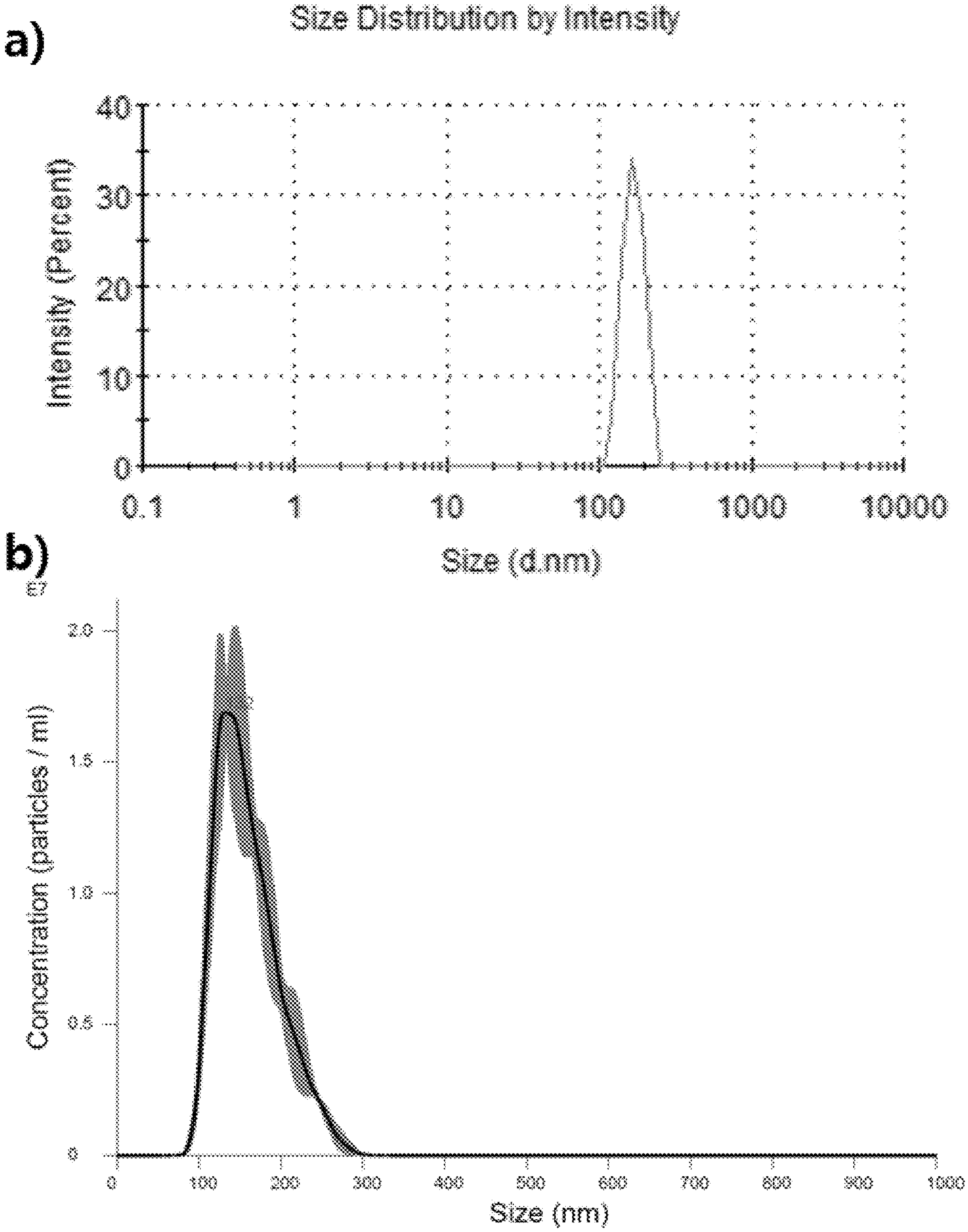

【Fig. 4b】
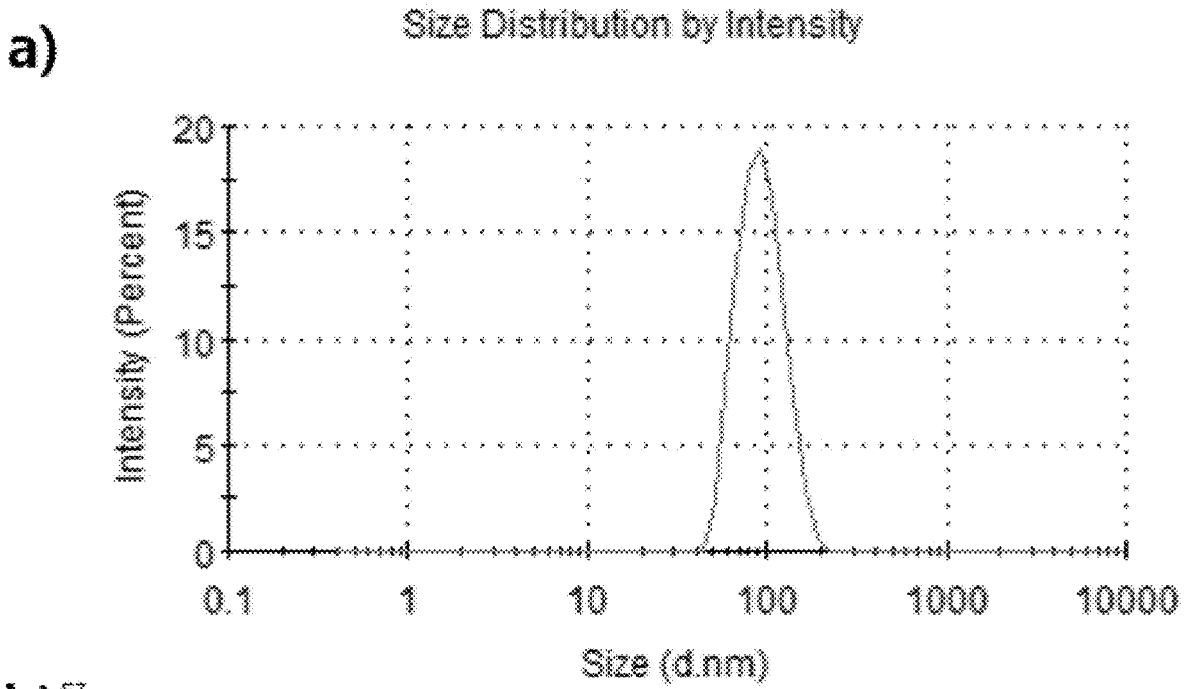
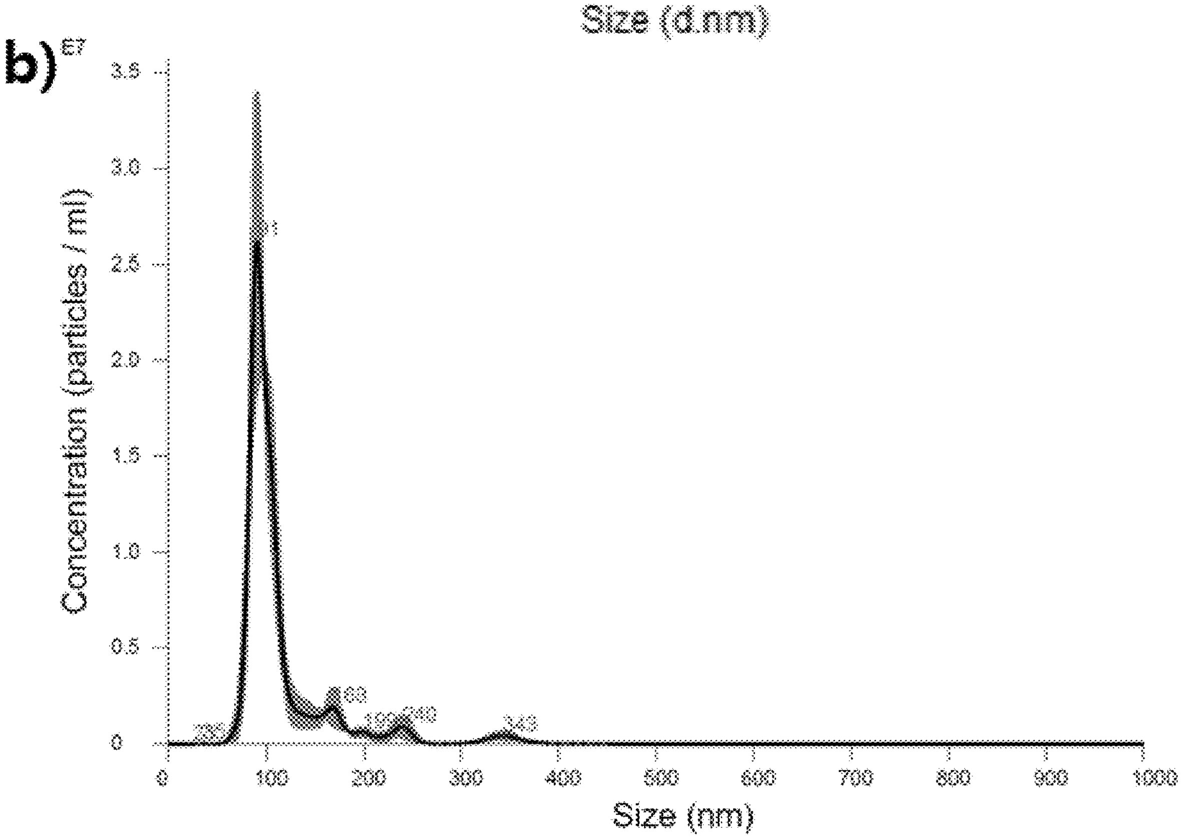

【Fig. 5a】
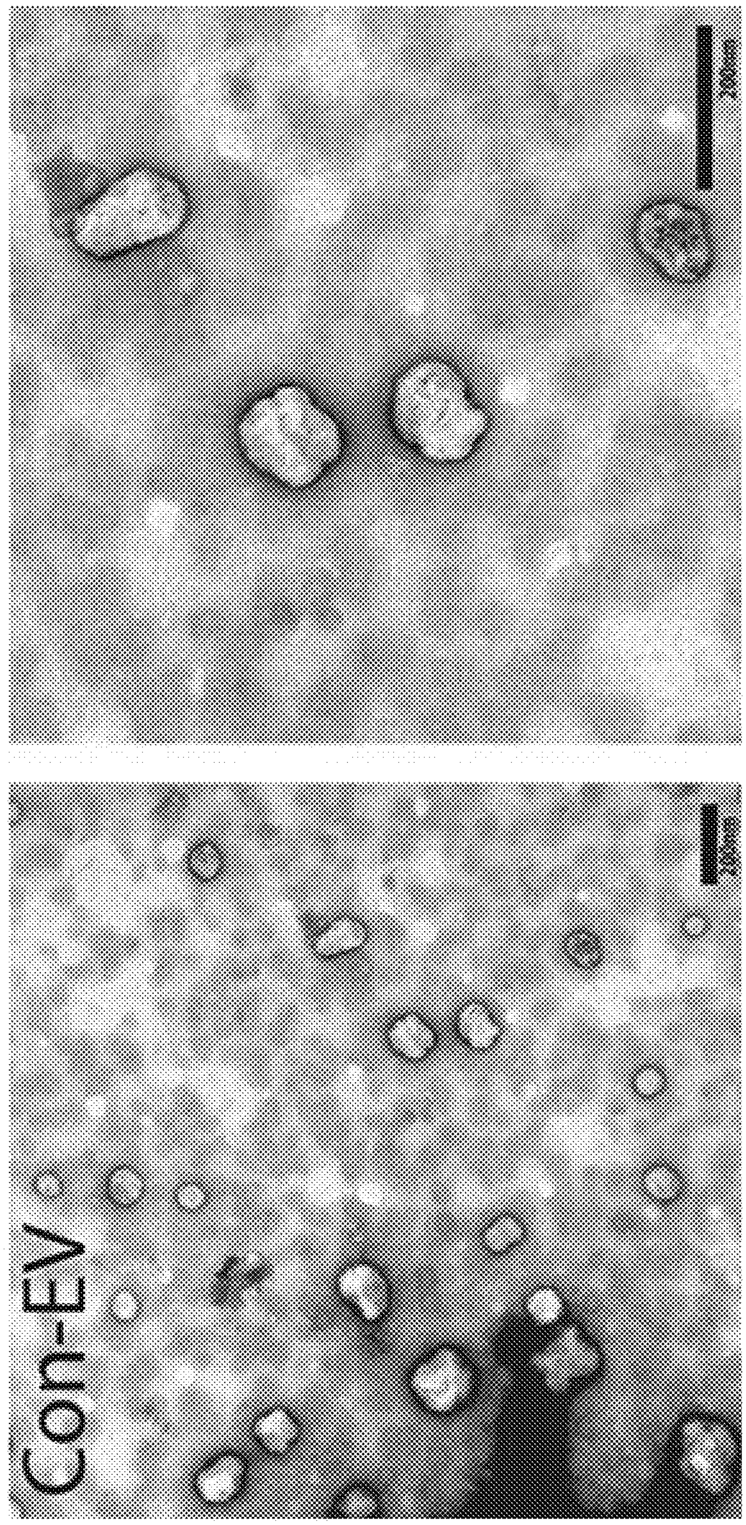

【Fig. 5b】
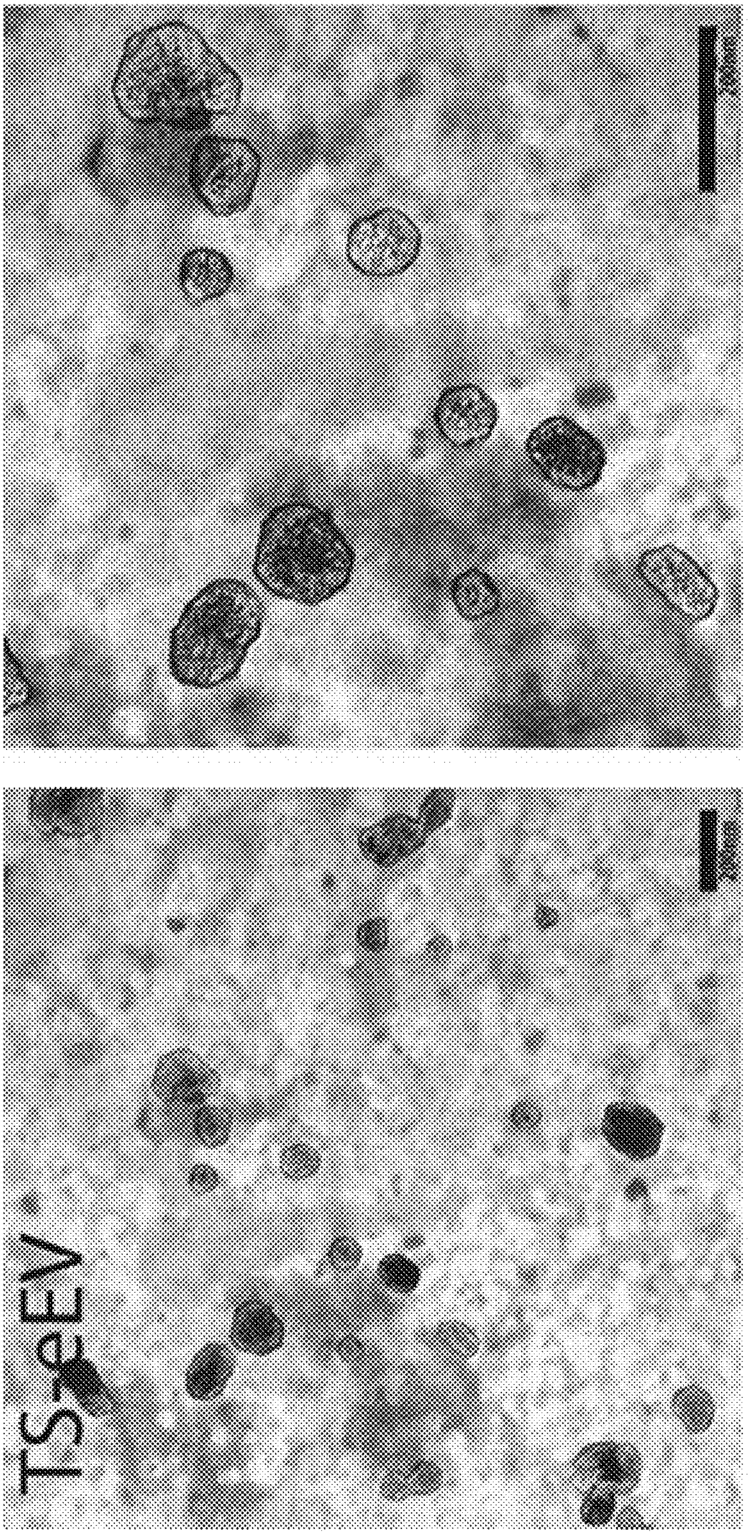

【Fig. 6】
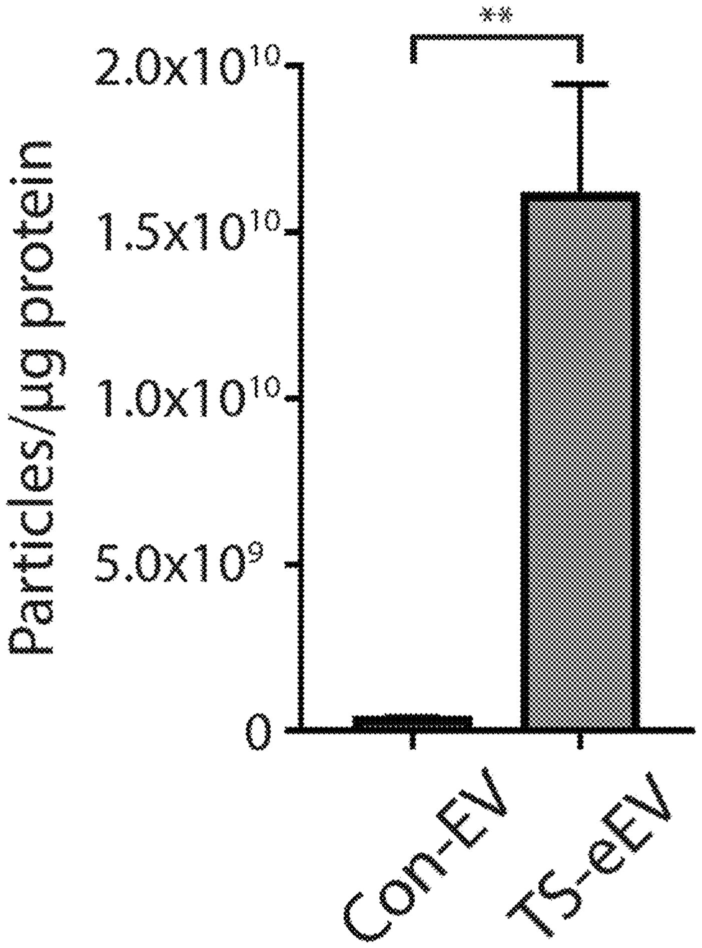

【Fig. 7a】
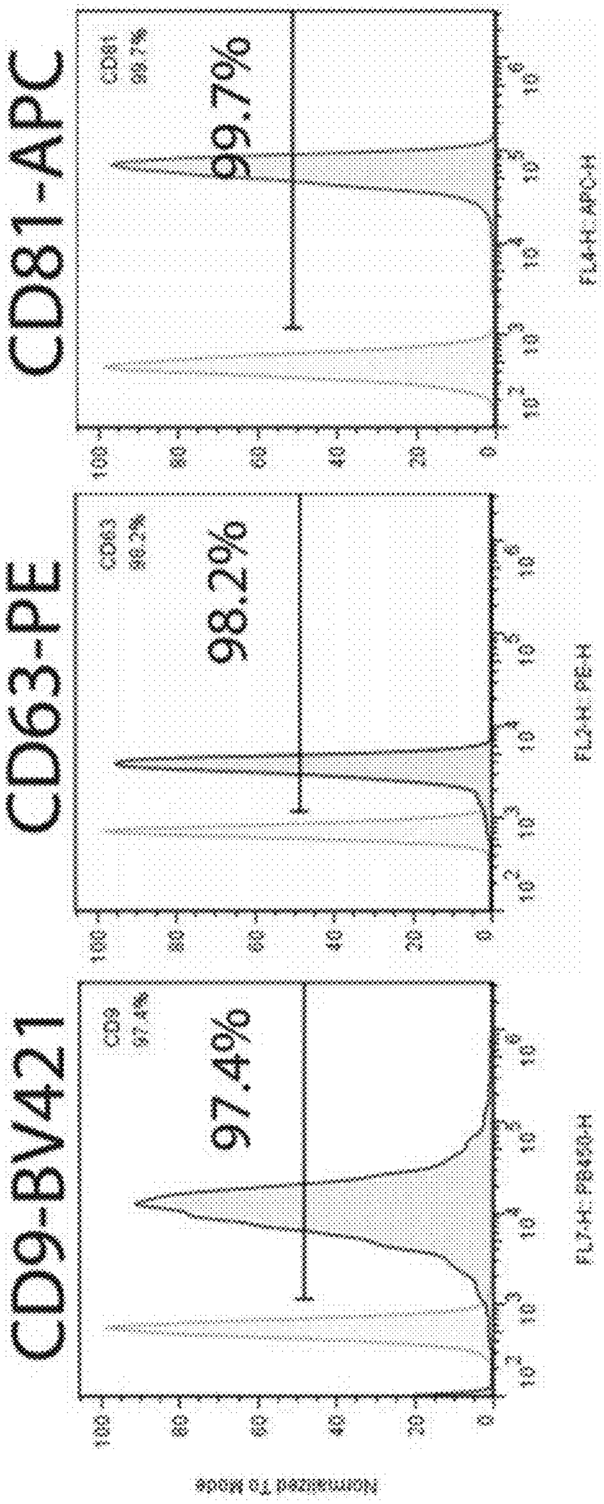

【Fig. 7b】
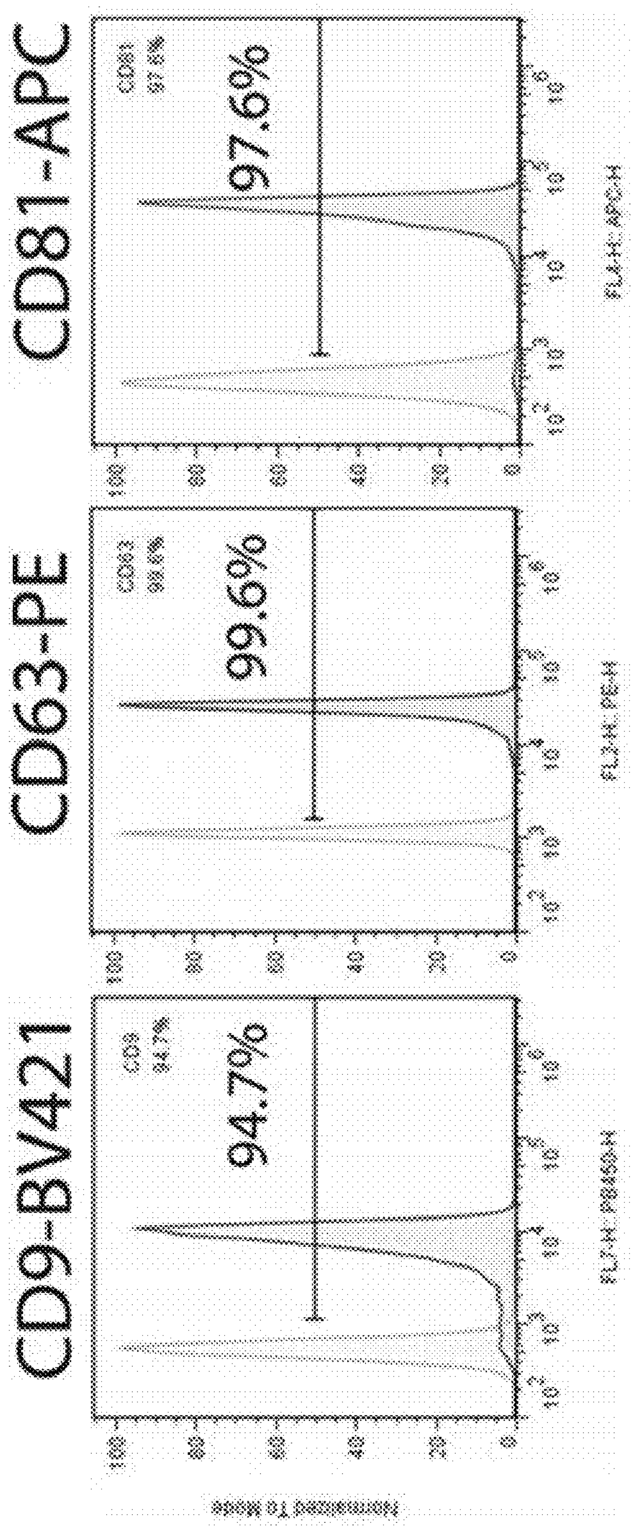

【Fig. 8】
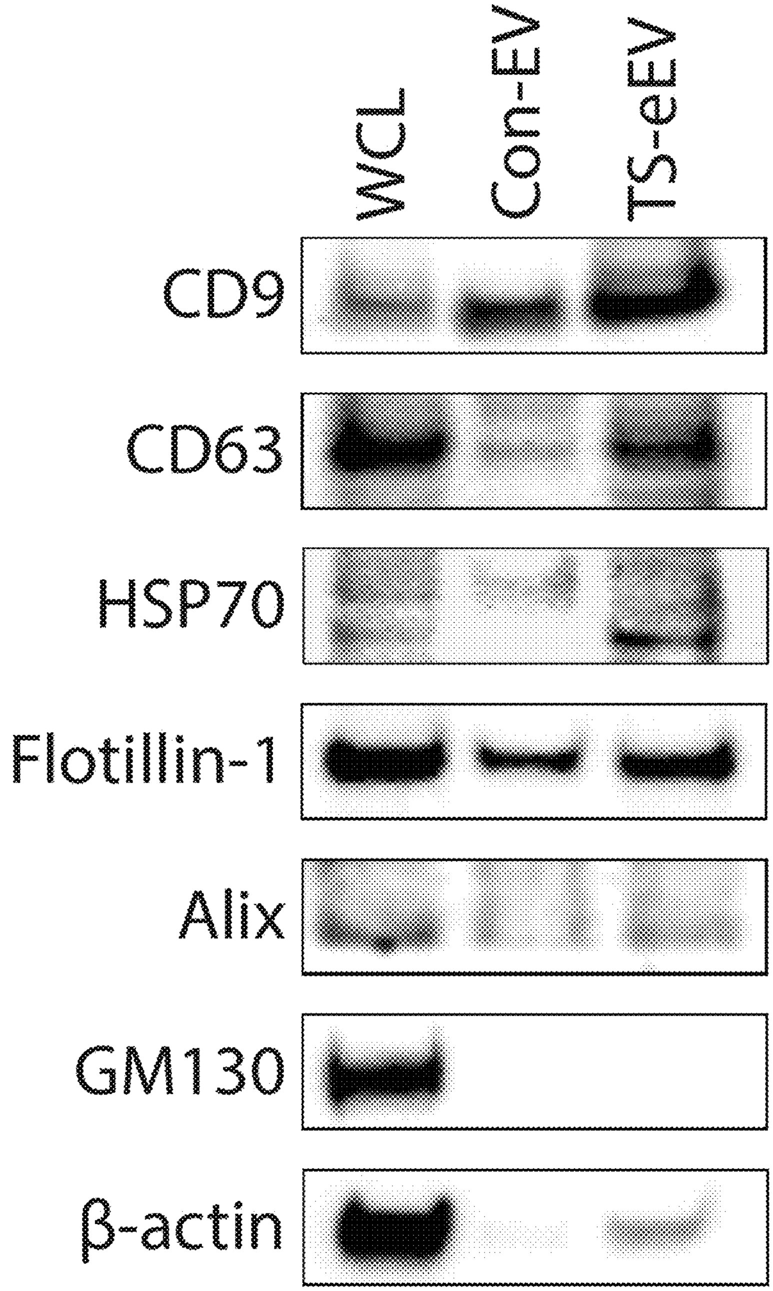

【Fig. 9】
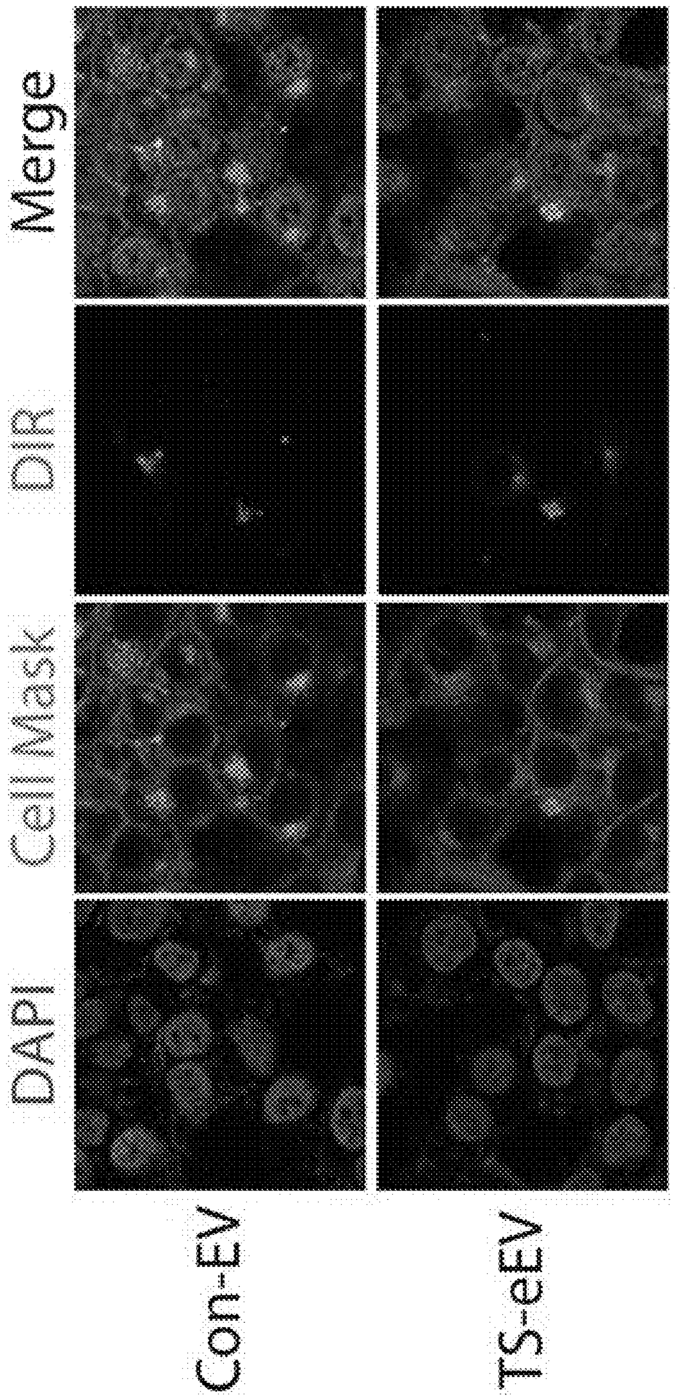

【Fig. 10】
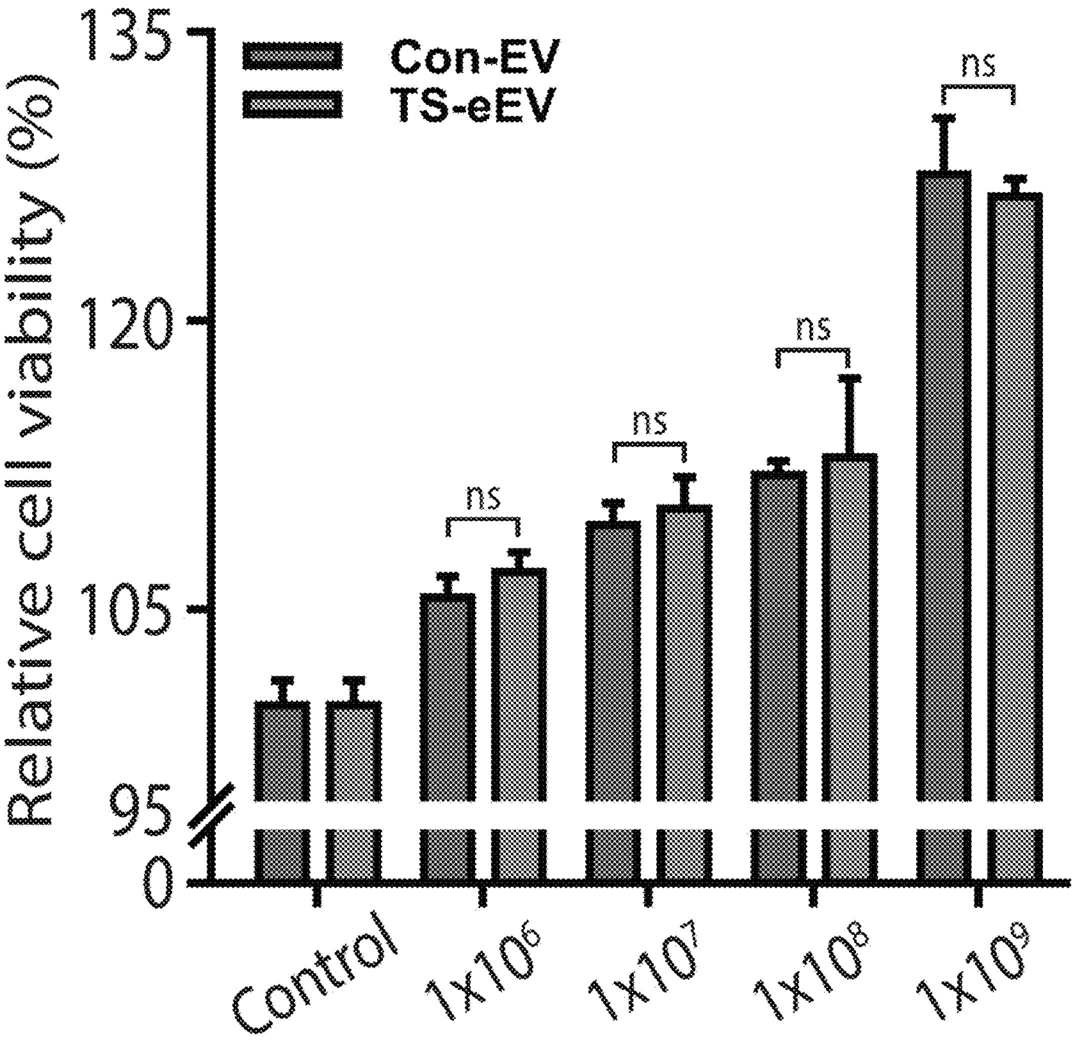

【Fig. 11a】
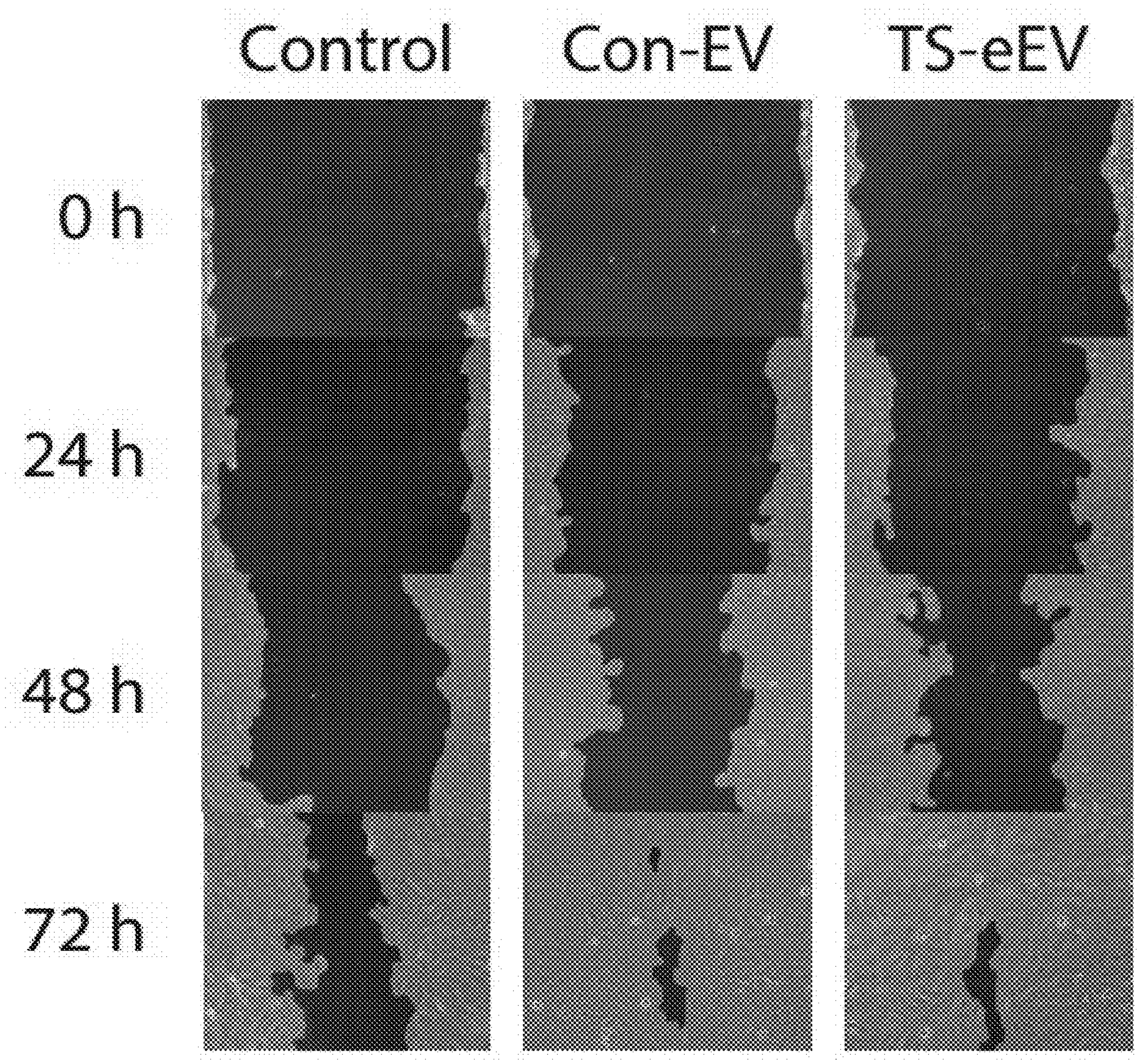

【Fig. 11b】
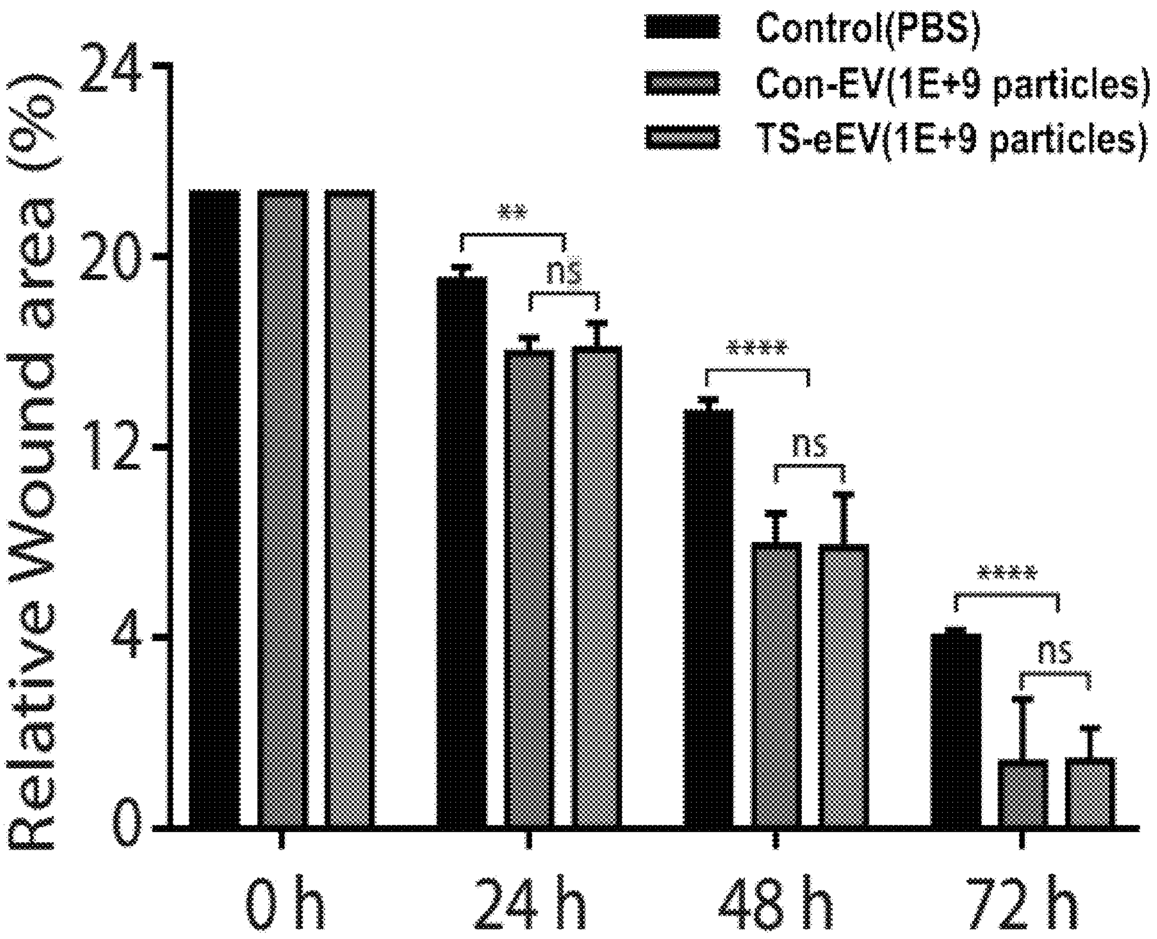

【Fig. 12a】
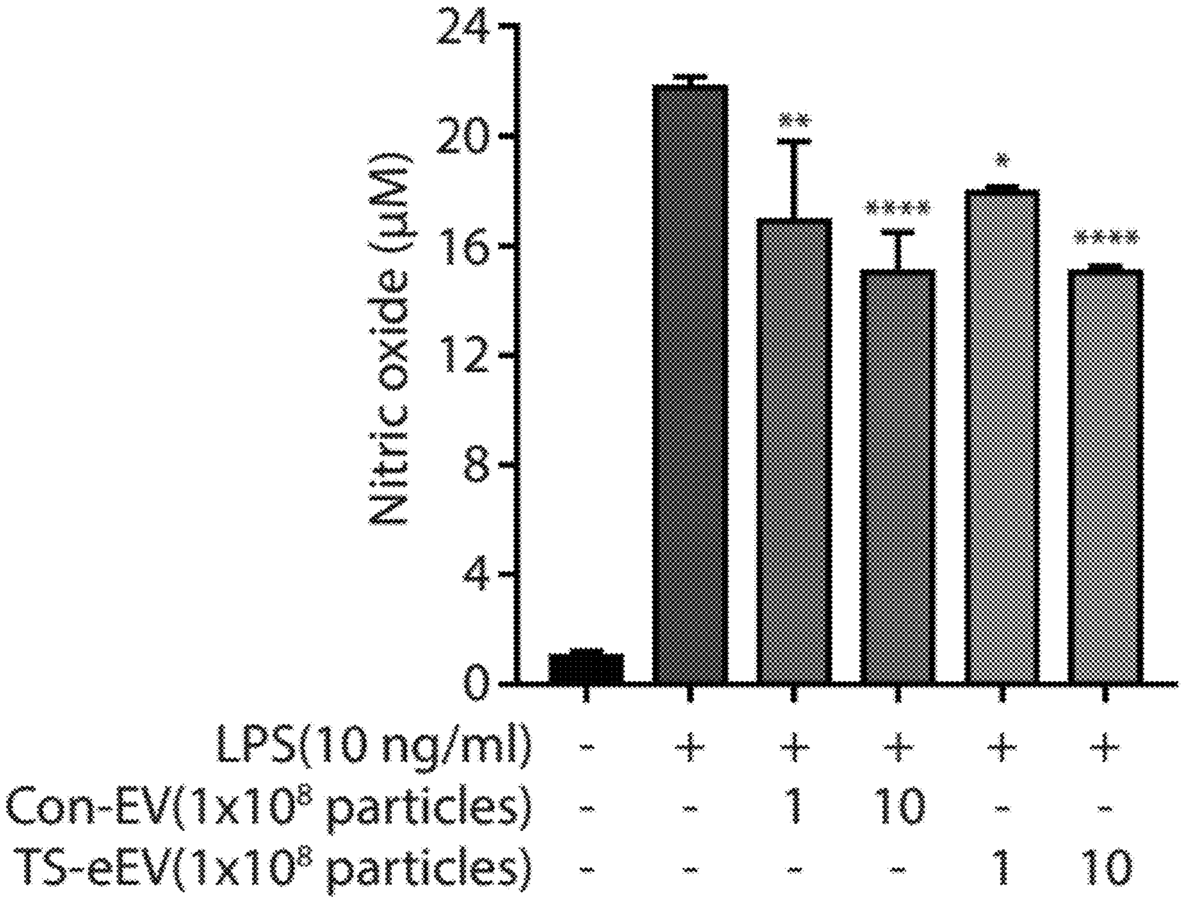

【Fig. 12b】
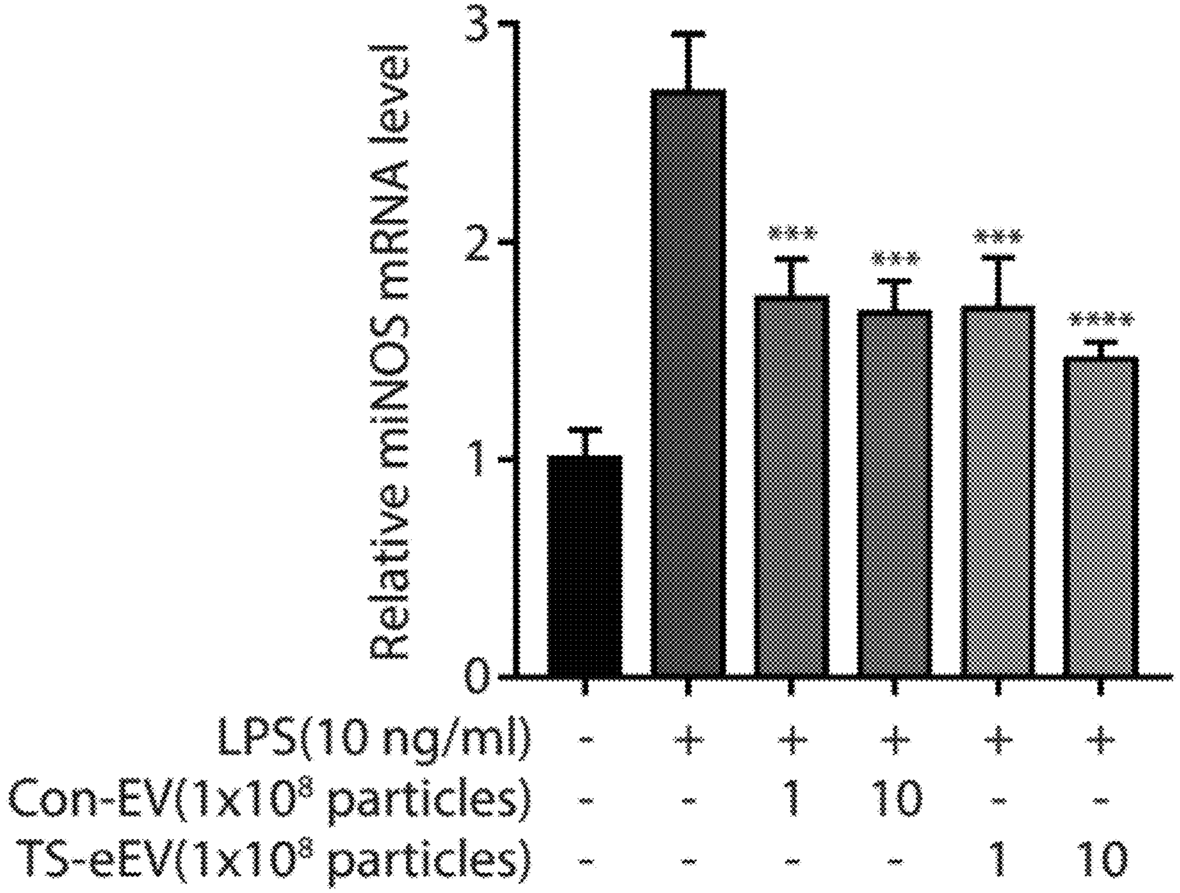

【Fig. 12c】
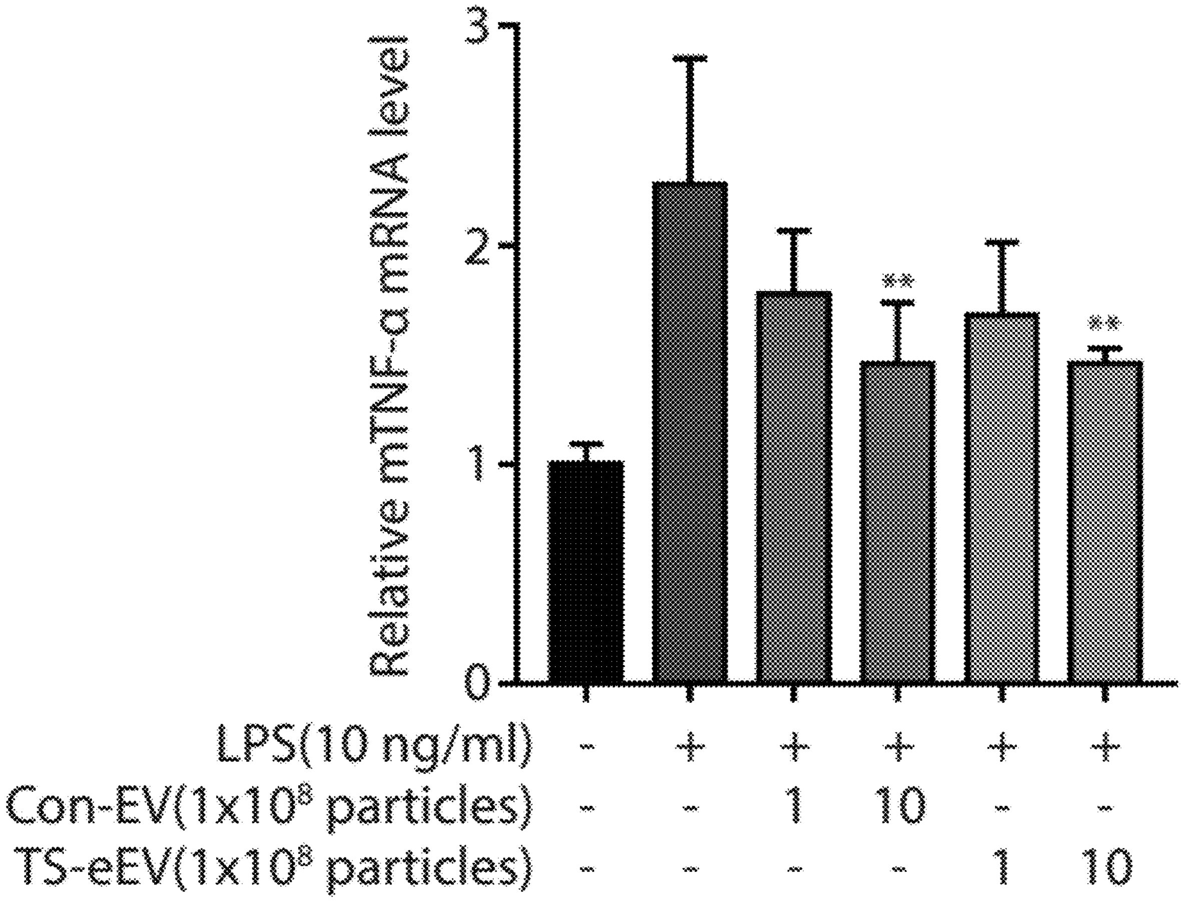

【Fig. 12d】
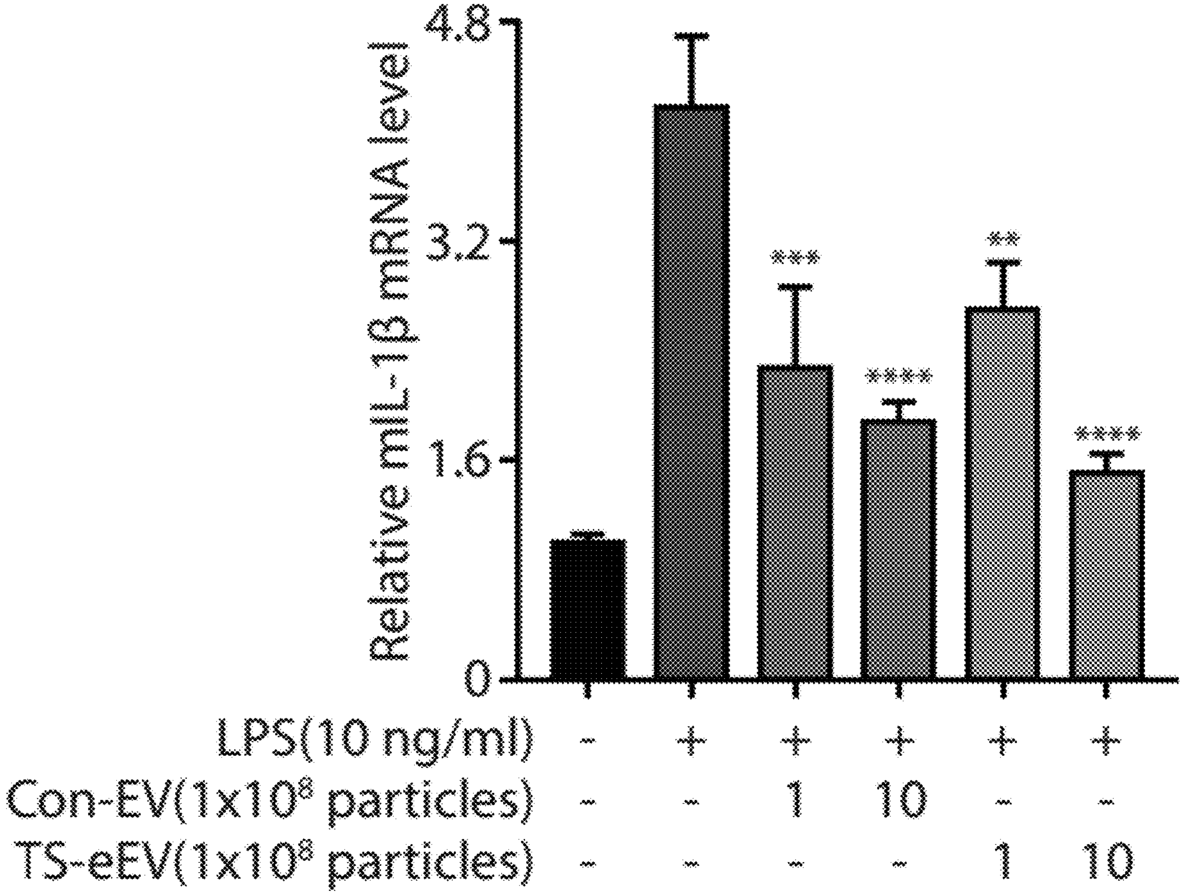

【Fig. 12e】
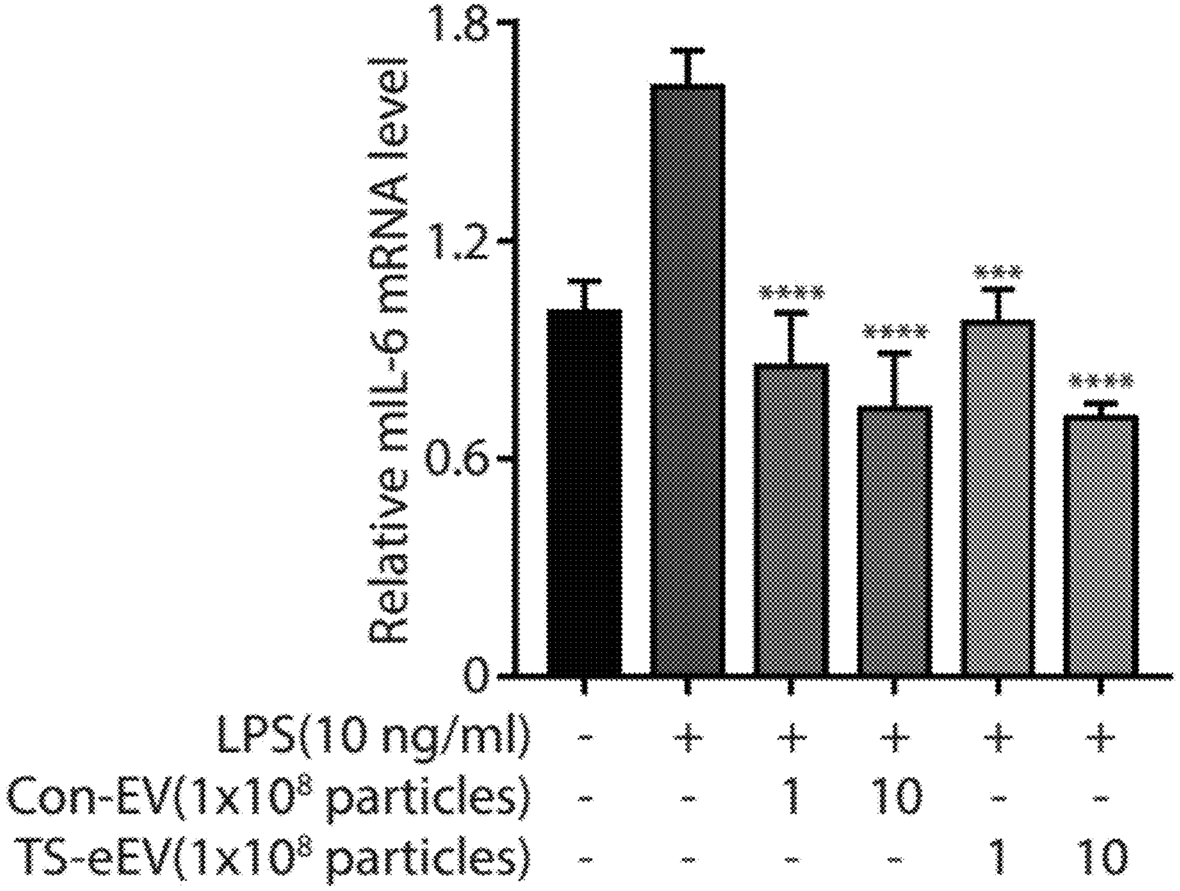

【Fig. 12f】
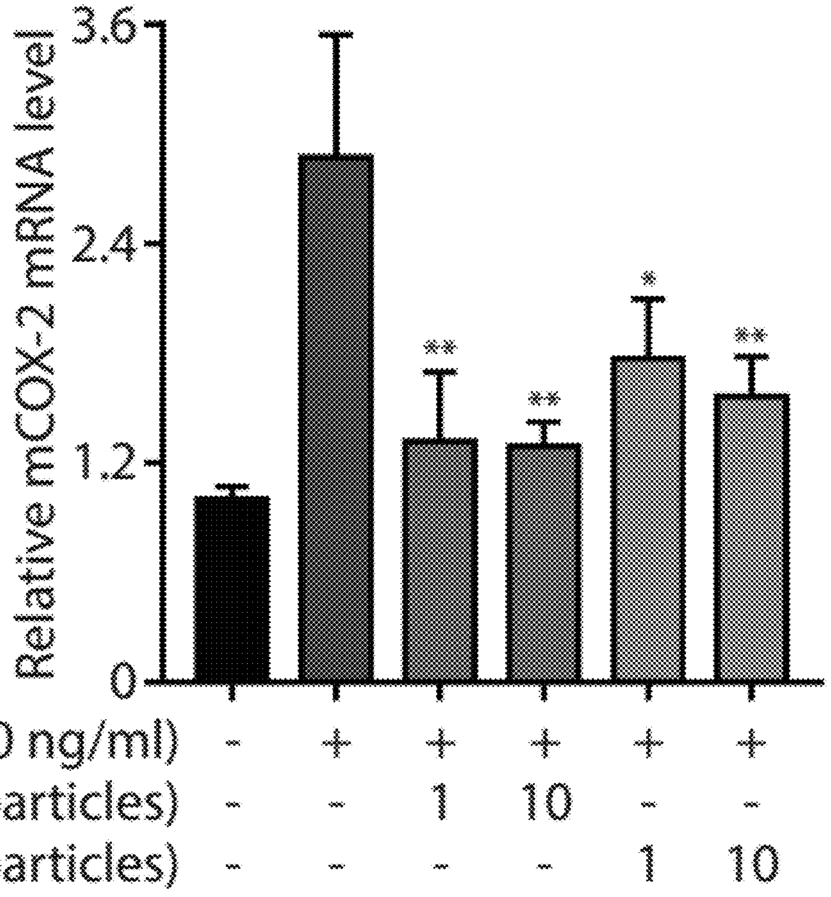

【Fig. 13】
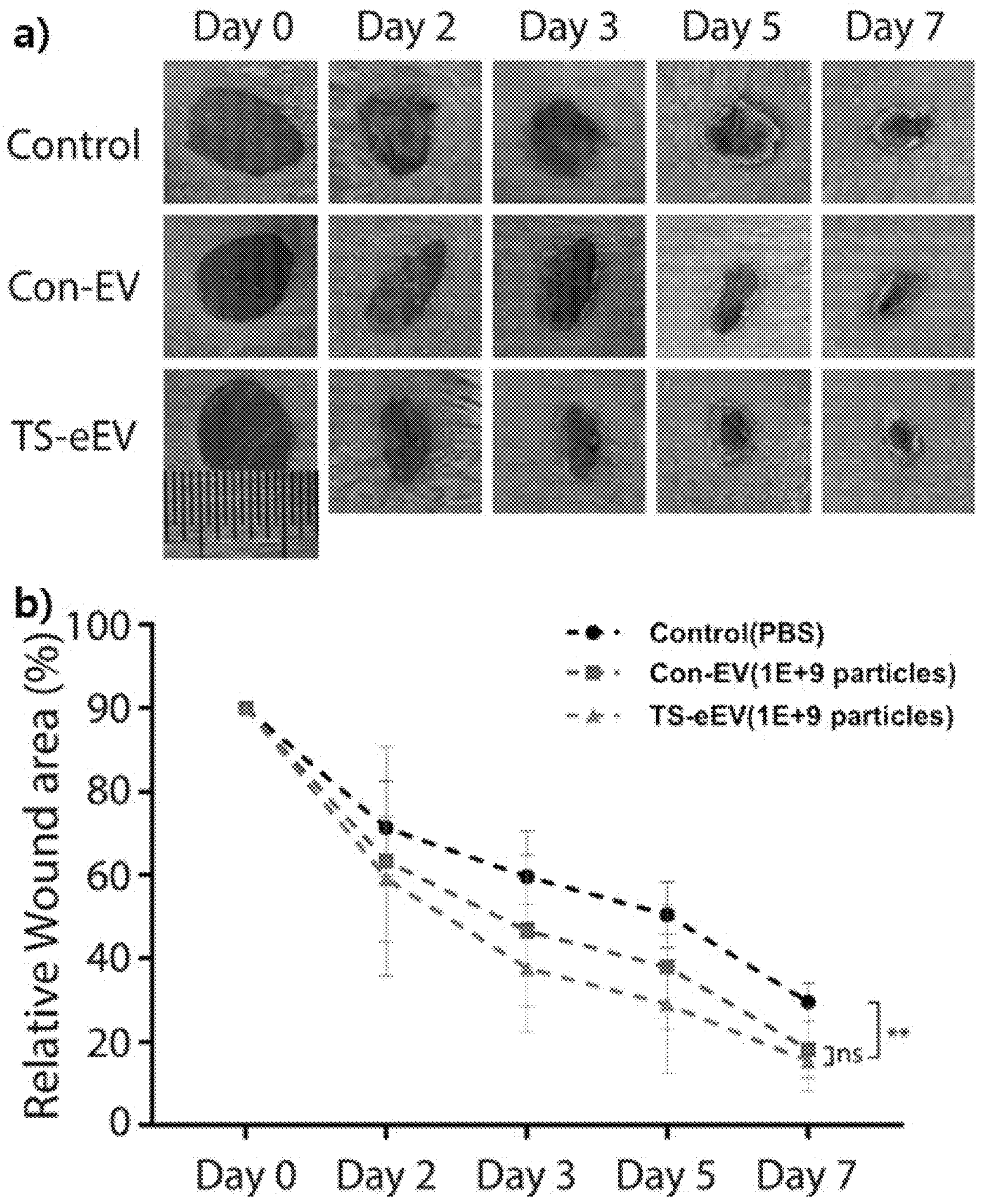

【Fig. 14a】
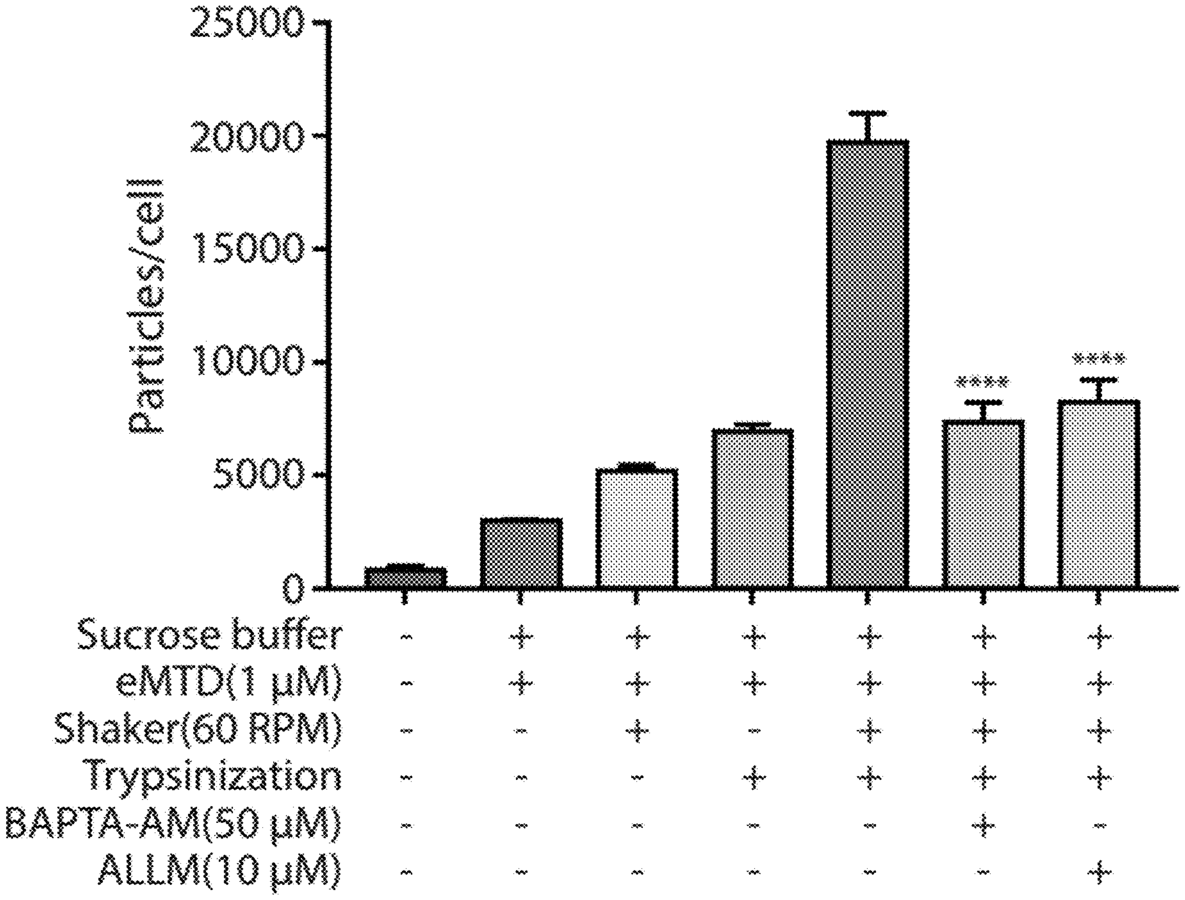

【Fig. 14b】
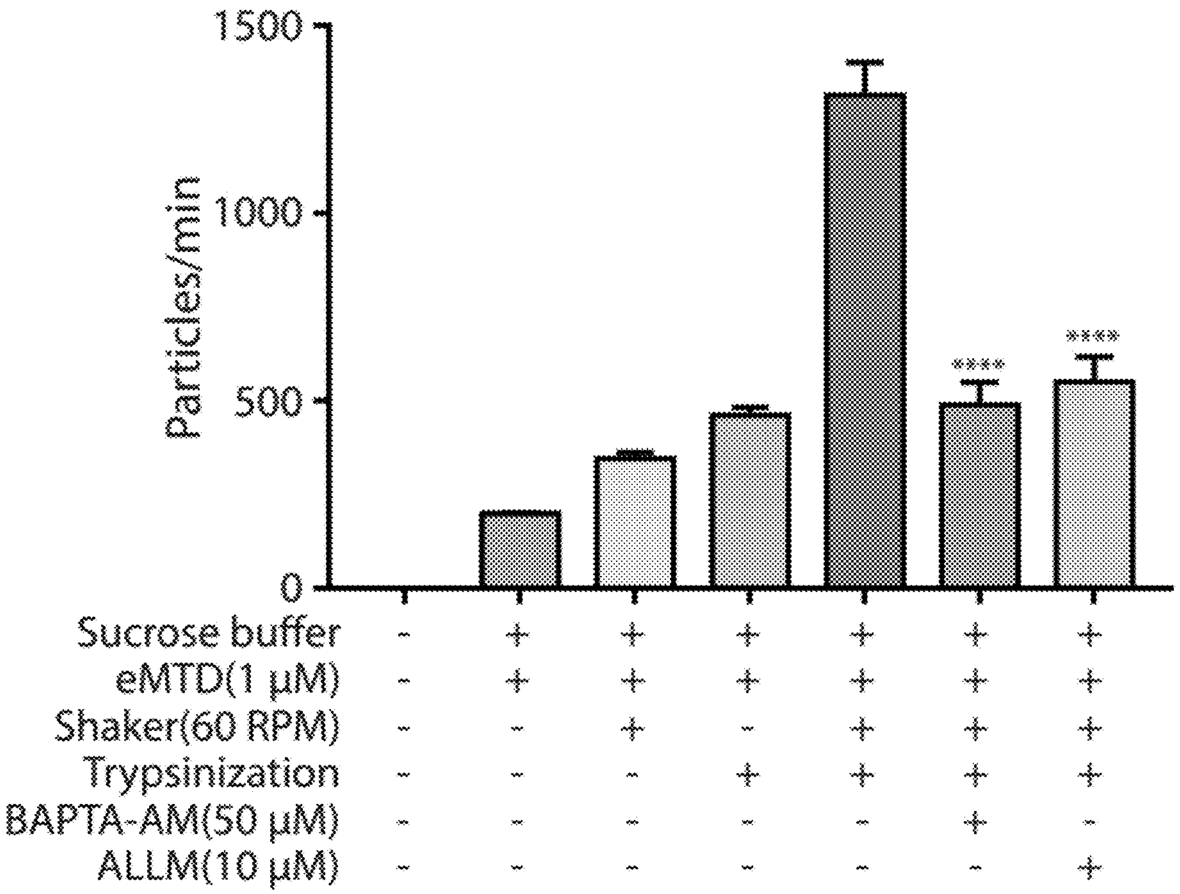

SEQUENCE LISTING

```
<160> NUMBER OF SEQ ID NOS: 11

<210> SEQ ID NO 1
<211> LENGTH: 20
<212> TYPE: PRT
<213> ORGANISM: Artificial Sequence
<220> FEATURE:
<223> OTHER INFORMATION: eMTD

<400> SEQUENCE: 1

Lys Leu Asn Phe Arg Gln Lys Leu Leu Asn Leu Ile Ser Lys Leu Phe
1               5                   10                  15

Cys Ser Gly Thr
            20


<210> SEQ ID NO 2
<211> LENGTH: 22
<212> TYPE: DNA
<213> ORGANISM: Artificial Sequence
<220> FEATURE:
<223> OTHER INFORMATION: miNOS Forward primer sequence

<400> SEQUENCE: 2

gagacaggga agtctgaagc ac                                              22


<210> SEQ ID NO 3
<211> LENGTH: 22
<212> TYPE: DNA
<213> ORGANISM: Artificial Sequence
<220> FEATURE:
<223> OTHER INFORMATION: miNOS Reverse primer sequence

<400> SEQUENCE: 3

ccagcagtag ttgctcctct tc                                              22


<210> SEQ ID NO 4
<211> LENGTH: 20
<212> TYPE: DNA
<213> ORGANISM: Artificial Sequence
<220> FEATURE:
<223> OTHER INFORMATION: mCOX2 Forward primer sequence

<400> SEQUENCE: 4

ttccagccca ttgaacctgg                                                 20


<210> SEQ ID NO 5
<211> LENGTH: 21
<212> TYPE: DNA
<213> ORGANISM: Artificial Sequence
<220> FEATURE:
<223> OTHER INFORMATION: mCOX2 Reverse primer sequence

<400> SEQUENCE: 5

gctacgaaaa cccaatcagc g                                               21


<210> SEQ ID NO 6
<211> LENGTH: 22
<212> TYPE: DNA
<213> ORGANISM: Artificial Sequence
```

-continued

```
<220> FEATURE:
<223> OTHER INFORMATION: mIL-6 Forward primer sequence

<400> SEQUENCE: 6

taccacttca caagtcggag gc                                          22


<210> SEQ ID NO 7
<211> LENGTH: 23
<212> TYPE: DNA
<213> ORGANISM: Artificial Sequence
<220> FEATURE:
<223> OTHER INFORMATION: mIL-6 Reverse primer sequence

<400> SEQUENCE: 7

ctgcaagtgc atcatcgttg ttc                                         23


<210> SEQ ID NO 8
<211> LENGTH: 20
<212> TYPE: DNA
<213> ORGANISM: Artificial Sequence
<220> FEATURE:
<223> OTHER INFORMATION: mIL-1 beta Forward primer sequence

<400> SEQUENCE: 8

aaattgggcc atgaggctcc                                             20


<210> SEQ ID NO 9
<211> LENGTH: 22
<212> TYPE: DNA
<213> ORGANISM: Artificial Sequence
<220> FEATURE:
<223> OTHER INFORMATION: mIL-1 beta Reverse primer sequence

<400> SEQUENCE: 9

gttgagaggg ctagtgagaa gg                                          22


<210> SEQ ID NO 10
<211> LENGTH: 22
<212> TYPE: DNA
<213> ORGANISM: Artificial Sequence
<220> FEATURE:
<223> OTHER INFORMATION: mTNF-alpha Forward primer sequence

<400> SEQUENCE: 10

ggtgcctatg tctcagcctc tt                                          22


<210> SEQ ID NO 11
<211> LENGTH: 23
<212> TYPE: DNA
<213> ORGANISM: Artificial Sequence
<220> FEATURE:
<223> OTHER INFORMATION: mTNF-alpha Reverse primer sequence

<400> SEQUENCE: 11

gccatagaac tgatgagagg gag                                         23
```

METHOD FOR MASS PRODUCTION OF HIGHLY PURE, STEM CELL-DERIVED EXTRACELLULAR VESICLE BY USING PEPTIDE

SEQUENCE LISTING

The instant application contains a Sequence Listing which has been submitted electronically in ASCII format and is hereby incorporated by reference in its entirety. Said ASCII copy, created on Jun. 13, 2023, is named 51712-039001_Sequence_Listing_6_13_23_ST25 and is 2,752 bytes in size.

TECHNICAL FIELD

This application claims priority to and the benefit of Korean Application Number 10-2020-0174891, filed in the Korean Intellectual Property Office on Dec. 14, 2020, the entire content of which is incorporated herein by reference.

The present disclosure relates to a method for mass production of extracellular vesicles, using a peptide derived from Noxa protein and mesenchymal stem cells and, specifically, a method for mass production of extracellular vesicles, wherein mesenchymal stem cells are cultured in a medium composition containing a Noxa protein-derived peptide, glucose, sucrose, and 3-(N-morpholino)propanesulfonic acid (MOPS), whereby extracellular vesicles having wound healing and immunomodulatory effects can be obtained with high purity at high yield.

BACKGROUND ART

Extracellular vesicles are lipid bilayer-structured vesicles with various sizes, secreted from various eukaryotic cells, such as insects, plants, and microorganisms as well as humans and animals. Of them, vesicles in nano-sizes are called exosomes.

Exosomes retain specific molecules such as proteins, nucleic acids, lipids, and carbohydrates that are contained in cells, stably protect the specific molecules with the lipid bilayer, and play a role in transmitting information to other cells after being released.

Exosomes are attracting attention as a new drug delivery vehicle. Exosomes not only enter cells more easily than liposomes, but also encounter little resistance from the immune system. In addition, an abundant amount of ligands present on the membrane surface of exosomes exhibits the possibility of cell-specific delivery through receptors.

In relation to a regenerative medicine or immune disease treatment using stem cells, a therapy using stem cell-derived extracellular vesicles, which replaces a cell therapy designed to transplant live stem cells into a lesion, is showing efficacy in preclinical trials. Cases have also been reported to enter the clinical stage with regard to the treatment of some diseases. Exosomes released from stem cells are known to contain key factors associated with anti-inflammatory and self-renewal activities that stem cells retain.

Therefore, the therapy employing no cells has attracted intensive attention as a new approach capable of surmounting the disadvantages of existing cell therapies, such as securing and maintaining a therapeutically effective amount of cells.

However, as a rule, nucleated cells each release only about 1,000 exosomes. Therefore, it is very important in the therapeutic technology using exosomes to improve the yield of exosomes separated from cells.

On the whole, exosomes are obtained by separation from a cell culture. Stem cells are generally cultured in a 2D manner and the acquirement of a large amount of exosomes in such a manner needs culturing of a large amount of cells, resulting in an increase in cost.

In addition, the separation of exosomes from a large volume of the cell culture in which a large number of cells has been cultured requires considerable labor. Centrifugation and tangential flow filtration (TFF) are mainly used for separation and purification of exosomes.

Encountering the problem of limited applicable capacity, centrifugation is not suitable for separating exosomes from large volumes of cell cultures. TFF has the advantage of being suitable for a large-scale process compared to centrifugation, but suffers from various disadvantages including the shear stress generated during the filtration process, and loss of exosomes.

In order to solve this problem, there is a need for development of an efficient extraction method capable of obtaining a large amount of exosomes from a small number of cells and a small volume of a cell culture medium.

DETAILED DESCRIPTION OF THE INVENTION

Technical Problem

The present inventors have conducted thorough and intensive research to develop a method for efficiently obtaining mesenchymal stem cell-derived extracellular vesicles, especially extracellular vesicles derived from mesenchymal stem cells from the umbilical cord, which contain various beneficial components and are composed of a lipid bilayer, thus functioning as a stable drug delivery system.

As a result, mesenchymal stem cells derived from the umbilical cord (Wharton's jelly-derived MSCs, WJ-MSCs) were cultured in a medium containing Noxa protein-derived peptides in an orbital shaking culture manner to obtain floating single cells. The extracellular vesicles can be separated from the cell suspension at high yield with high purity and were found to exhibit stem cell-intrinsic wound healing and immunomodulatory effects.

Accordingly, an aspect of the present disclosure is to provide a method for producing mesenchymal stem cell-derived extracellular vesicles.

Another aspect of the present disclosure is to provide extracellular vesicles isolated from mesenchymal stem cells pretreated with a medium composition including a peptide composed of the amino acid sequence of SEQ ID NO: 1, glucose, sucrose, and MOPS, or a culture thereof.

A further aspect of the present disclosure is to provide a pharmaceutical composition including extracellular vesicles isolated from mesenchymal stem cells or a culture thereof for alleviation, suppression, or treatment of wound.

A yet further aspect of the present disclosure is to provide a pharmaceutical composition including extracellular vesicles isolated from mesenchymal stem cells or a culture thereof for alleviation, suppression, or treatment of inflammation.

A yet another aspect of the present disclosure is to provide a food composition including extracellular vesicles isolated from mesenchymal stem cells or a culture thereof for alleviation, suppression, or amelioration of an inflammatory disease.

Technical Solution

The present disclosure is drawn to a method for mass production of extracellular vesicles, using a peptide derived from Noxa protein and mesenchymal stem cells derived from the umbilical cord and, specifically, to a method for mass production of extracellular vesicles, wherein mesenchymal stem cells are cultured in a medium composition containing a Noxa protein-derived peptide, glucose, sucrose, and 3-(N-morpholino)propanesulfonic acid (MOPS), whereby extracellular vesicles having wound healing and immunomodulatory effects can be obtained with high purity at high yield.

Below, a detailed description will be given of the present disclosure.

An aspect of the present disclosure pertains to a method for production of mesenchymal stem cell-derived extracellular vesicles, the method including:

a first culturing step of pre-culturing mesenchymal stem cells; and a second culturing step of culturing the pre-cultured mesenchymal stem cells in a medium composition containing a peptide composed of the amino acid sequence of SEQ ID NO: 1, glucose, sucrose, and 3-(N-morpholino)propanesulfonic acid [MOPS].

In the present disclosure, the mesenchymal stem cells may be derived from at least one selected from the group consisting of bone marrow, embryo, umbilical cord, muscle, fat, and nerve tissue, for example, from the umbilical cord, but with no limitations thereto.

As used herein, the term "stem cells" refers to undifferentiated cells that self-renew and have the ability to differentiate into two or more different cell types.

In an embodiment of the present disclosure, the mesenchymal stem cells may be mesenchymal stem cells derived from the umbilical cord (Wharton's jelly-derived MSCs, WJ-MSCs).

The stem cells may be autologous or homologous stem cells, may be derived from any type of animals including human and non-human mammals, and may originate from an adult or an embryo, but with no limitations thereto.

In the present disclosure, the extracellular vesicles may be classified into the following three types according to the size and generation process thereof: Exosome; Apoptotic body; and Microveslcle (Ectosome).

As used herein, the term "exosome" refers to a cell-derived vesicle and exosomes are present in almost all eukaryotic body fluids.

In the present disclosure, exosomes each range in diameter from 30 to 100 nm, which is larger LDL proteins and much smaller than erythrocytes, but with no limitations thereto.

In the present disclosure, the peptide composed of the amino acid sequence of SEQ ID NO: 1 may be a Noxa protein-derived peptide.

The Bcl-2 homology 3 (BH3) domain of Noxa protein binds Mcl-1 and Bcl2A1 to inactivate their anti-apoptotic activities, which, in turn, activates BAX and BAK proteins, causing cytochrome-c to leak into the cytosol, where the caspase system completes the apoptotic process.

As used herein, the term "peptide" refers to a linear molecule which is formed as amino acid residues are bonded to each other via a peptide bond.

In one embodiment of the present disclosure, the Noxa protein-derived peptide may be a peptide having a homology of about 60% or more, about 70% or more, about 80% or more, about 90% or more, about 95% or more, about 98% or more, or about 99% or more with the peptide composed of the amino acid sequence of SEQ ID NO: 1.

The peptide in the present disclosure may be directly synthesized in a chemical manner using solid-phase peptide synthesis, for example, using an automated peptide synthesizer or may be biologically prepared by inserting DNA encoding the peptide a vector and expressing, but with no limitations thereto.

As used herein, the term "vector" refers to a means for expressing a gene of interest in a host cell.

Examples of the vector include plasmid vectors, cosmid vectors, and viral vectors such as bacteriophage vectors, adenovirus vectors, retroviral vectors, and adeno-associated virus vectors, but are not limited thereto.

The term "pre-culturing", as used herein, refers to culturing mesenchymal stem cells to a predetermined level of confluency, for example, 50% or higher, 60% or higher, 70% or higher, 80% or higher, or 90% or higher confluency, but with no limitations thereto.

In an embodiment of the present disclosure, the first culturing step may further include a trypsin treatment step of treating the pre-cultured mesenchymal stem cells with trypsin to float the mesenchymal stem cells, but with no limitations thereto.

In an embodiment of the present disclosure, the first culturing step may further include an acquiring step of performing centrifugation to collect the pre-cultured mesenchymal stem cells, but with no limitations thereto.

In the present disclosure, the medium composition contains the peptide composed of the amino acid sequence of SEQ ID NO: 1 at a concentration of 0.1 to 5.0 uM, 0.1 to 4.5 uM, 0.1 to 4.0 uM, 0.1 to 3.5 uM, 0.1 to 3.0 uM, 0.1 to 2.5 uM, 0.1 to 2.0 uM, 0.1 to 1.5 uM, 0.5 to 5.0 uM, 0.5 to 4.5 uM, 0.5 to 4.0 uM, 0.5 to 3.5 uM, 0.5 to 3.0 uM, 0.5 to 2.5 uM, 0.5 to 2.0 uM, or 0.5 to 1.5 uM, and for example, 0.5 to 1.5 uM, but with no limitations thereto.

In the present disclosure, the medium composition contains glucose at a concentration of 1 to 10 mM, 1 to 8 mM, 1 to 6 mM, 2 to 10 mM, 2 to 8 mM, 2 to 6 mM, 3 to 10 mM, 3 to 8 mM, 3 to 6 mM, 4 to 10 mM, 4 to 8 mM, or 4 to 6 mM, for example, 4 to 6 mM, but with no limitations thereto.

In the present disclosure, the medium composition contains sucrose at a concentration of 200 to 300 mM, 200 to 280 mM, 200 to 260 mM, 220 to 300 mM, 220 to 280 mM, 220 to 260 mM, 240 to 300 mM, 240 to 280 mM, or 240 to 260 mM, for example, 240 to 260 mM, but with no limitations thereto.

In the present disclosure, the medium composition contains 3-(N-morpholino)propanesulfonic acid [MOPS] at a concentration of 1 to 20 mM, 1 to 18 mM, 1 to 16 mM, 1 to 14 mM, 1 to 12 mM, 3 to 20 mM, 3 to 18 mM, 3 to 16 mM, 3 to 14 mM, 3 to 12 mM, 5 to 20 mM, 5 to 18 mM, 5 to 16 mM, 5 to 14 mM, 5 to 12 mM, 8 to 20 mM, 8 to 18 mM, 8 to 16 mM, 8 to 14 mM, or 8 to 12 mM, for example, 8 to 12 mM, but with no limitations thereto.

In the present disclosure, the second culturing step is adapted for culturing the pre-cultured mesenchymal stem cells in a medium composition including a peptide consisting of the amino acid sequence of SEQ ID NO: 1, glucose, sucrose, and 3-(N-morpholino)propanesulfonic acid [MOPS], but with no limitations thereto.

In the present disclosure, the second culturing step may be carried out for 5 to 30 minutes, 5 to 25 minutes, 5 to 20 minutes, 5 to 18 minutes, 10 to 30 minutes, 10 to 25 minutes, 10 to 20 minutes, 10 to 18 minutes, 13 to 30 minutes, 13 to 25 minutes, 13 to 20 minutes, or 13 to 18 minutes, for example, 13 to 18 minutes, but with no limitations thereto.

In an embodiment of the present disclosure, the second culturing step may be performed in an orbital shaking culture manner.

As used herein, the term "orbital shaking culture" refers to culturing cells in, for example, a flask on a plate that is horizontally rotating in a circle of a predetermined radius at a constant speed, but with no limitations thereto.

In an embodiment of the present disclosure, the orbital shaking culture may be performed using an orbital shaker.

In an embodiment of the present disclosure, the production method may further include an isolation step of isolating the mesenchymal stem cell-derived extracellular vesicles, but with no limitations thereto.

In the present disclosure, the isolation step may be adapted for obtaining extracellular vesicles from the medium composition that has undergone the second culturing step, but with no limitations thereto.

In an example of the present disclosure, when cultured in the medium composition containing a peptide composed of the amino acid sequence of SEQ ID NO: 1, glucose, sucrose, and MOPS, mesenchymal stem cells were measured to produce an increased number of total particles, compared to the control (Table 8).

In an embodiment of the present disclosure, when cultured in an orbital shaking culture manner in the medium composition containing a peptide composed of the amino acid sequence of SEQ ID NO: 1, glucose, sucrose, and MOPS, mesenchymal stem cells were measured to produce an increased number of total particles, compared to the control or those cultured in a non-orbital shaking culture manner (Table 8).

In an embodiment of the present disclosure, when cultured in an orbital shaking culture manner in the medium composition containing a peptide composed of the amino acid sequence of SEQ ID NO: 1, glucose, sucrose, and MOPS, mesenchymal stem cells were measured to produce an increased number of total particles, compared to the control or those cultured in an orbital shaking culture manner or a non-orbital shaking culture manner (Table 8).

The method for producing extracellular vesicles according to the present disclosure can produce extracellular vesicles at high yield with high purity. In an embodiment of the present disclosure, the extracellular vesicles produced when culturing mesenchymal stem cells in an orbital shaking culture manner in the medium composition containing a peptide composed of the amino acid sequence of SEQ ID NO: 1, glucose, sucrose, and MOPS were observed to have greatly increased purity, compared to the control (FIG. 6 and Table 10).

Another aspect of the present disclosure is drawn to extracellular vesicles derived from mesenchymal stem cells pretreated with a peptide composed of the amino acid sequence of SEQ ID NO: 1, glucose, sucrose, and 3-(N-morpholino)propanesulfonic acid [MOPS].

In the present disclosure, the pre-treatment may refer to a process of treating stem cells with trypsin in advance.

In an embodiment of the present disclosure, the mesenchymal stem cells may be further pretreated with a medium composition containing a peptide composed of the amino acid sequence of SEQ ID NO: 1, glucose, sucrose, and MOPS.

In the present disclosure, the term "culture" may mean a culture supernatant after mesenchymal stem cells are cultured in a typical manner known in the art or a cell-suspended culture medium after mesenchymal stem cell are cultured in an orbital shaking culture manner, but with no limitations thereto.

The extracellular vesicles of the present disclosure may exhibit a palliative, suppressive, or healing effect on wound.

In an embodiment of the present disclosure, the extracellular vesicles isolated from mesenchymal stem cells pretreated with the medium composition or from a culture thereof were observed to exhibit relatively improved cell migration, compared to the control (FIG. 11 and Table 12).

Extracellular vesicles isolated from the mesenchymal stem cells or a culture thereof can exhibit a palliative, suppressive, or therapeutic effect on inflammatory diseases.

In an embodiment of the present disclosure, extracellular vesicles isolated from mesenchymal stem cells pretreated with the medium composition or a culture thereof are observed to reduce the level of nitric oxide (NO) and downregulate the mRNA expression of inflammation-inducing genes (iNOS, TNF-α, IL-1β, IL-6, COX-2) in LPS-induced inflammation models (FIG. 12 and Table 13).

Another aspect of the present disclosure is concerned with a pharmaceutical composition including extracellular vesicles derived from mesenchymal stem cells pretreated with a peptide composed of the amino acid sequence of SEQ ID NO: 1, glucose, sucrose, and 3-(N-morpholino)propanesulfonic acid [MOPS] for palliating, suppressing, or healing a wound.

As used herein, the term "wound" refers to a damaged site present in damaged tissues such as skin, organs, or bones.

In the present disclosure, the palliation, suppression, or healing of a wound may mean mitigating or inhibiting the degree of tissue damage or therapeutically treating a damaged tissue by, for example, a method of promoting cell differentiation in a damaged tissue, but with no limitations thereto.

In the present disclosure, the pharmaceutical composition for palliating, suppressing, or healing a wound may be a cell therapy product.

As used herein, the term "cell therapy product" refers to a therapeutic, diagnostic, and prophylactic medicine designed to restore the organization of cells and tissues through a series of actions responsible for modifying biological traits of cells by proliferating and selecting living autologous, allogenic, or xenogenic cells or by other methods.

In one embodiment of the present disclosure, the cell therapy product may be a stem cell therapy product.

In the present disclosure, the term "stem cell therapy product" may refer to a biopharmaceutical using autologous bone marrow-derived, autologous adipocyte-derived, or allogeneic cord blood-derived stem cells.

In the present disclosure, the pharmaceutical composition may include, as an active ingredient, exosomes isolated from mesenchymal stem cells or a culture thereof.

In the present disclosure, the pharmaceutical composition may include, as an active ingredient, an extracellular vesicle isolated from a mesenchymal stem cell pretreated with a peptide composed or the amino acid sequence of SEQ ID NO: 1, glucose, sucrose, and MOPS or from a culture thereof.

As used herein, the term "including as an active ingredient" means including extracellular vesicles isolated from stem cells or a culture thereof in an amount sufficient to achieve alleviation, inhibition, or therapeutic activity for a specific disease.

In the present disclosure, the pharmaceutical composition may include a pharmaceutically acceptable carrier, for example, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, etc., but is not limited thereto.

In the present disclosure, the pharmaceutical composition may further include a lubricant, a humectant, a sweetener agent, a flavorant, an emulsifier, a suspending agent, and a preservative, but is not limited thereto.

In the present disclosure, the pharmaceutical composition can be administered orally and parenterally, for example, through intravenous, subcutaneous, intramuscular, intraperitoneal, topical, intranasal, intrapulmonary, rectal, intrathecal, intraocular, dermal, and transdermal routes, but with no limitations thereto.

In the present disclosure, the administration dose of the pharmaceutical composition is determined to effectively achieve desired palliation, suppression, and therapy and may vary depending on various factors including formulation methods, administration modes, patient's age, weight, sex, pathological condition, and meal, the time of administration, the route of administration, excretion rates, and response sensitivity. For example, the daily dosage of the pharmaceutical composition of the present disclosure may be 0.0001-1000 mg/kg.

In the present disclosure, according to any conventional method easily implementable by one of ordinary skill in the art, the pharmaceutical composition may be formulated into a unit dosage form or enclosed in a multi-dose container, together with a pharmaceutically acceptable carrier and/or excipient. In this regard, the formulation may be a solution, a suspension, or an emulsion in oil or aqueous media, or a syrup, an extract, a pulvis, a granule, a tablet, or a capsule, which may further include a dispersing agent or a stabilizer, but with no limitations thereto.

Another aspect of the present disclosure is drawn to a pharmaceutical composition including extracellular vesicles derived from mesenchymal stem cells pretreated with a peptide composed of the amino acid sequence of SEQ ID NO: 1, glucose, sucrose, and 3-(N-morpholino)propanesulfonic acid [MOPS] for alleviation, suppression, or treatment of an inflammatory disease.

In the present disclosure, the inflammatory disease may be at least one selected from the group consisting of atopic dermatitis, edema, dermatitis, allergy, asthma, conjunctivitis, periodontitis, rhinitis, otitis media, sore throat, tonsillitis, pneumonia, gastric ulcer, gastritis, Crohn's disease, colitis, hemorrhoids, gout, ankylosing spondylitis, rheumatic fever lupus, fibromyalgia, psoriatic arthritis, osteoarthritis, rheumatoid arthritis, parotid arthritis, tendinitis, tendinitis, myositis, hepatitis, cystitis, nephritis, Sjogren's syndrome, and multiple sclerosis, but with no limitations thereto.

Another aspect of the present disclosure is drawn to a food composition including extracellular vesicles derived from mesenchymal stem cells pretreated with a peptide composed of the amino acid sequence of SEQ ID NO: 1, glucose, sucrose, and 3-(N-morpholino)propanesulfonic acid [MOPS].

In the present disclosure, the food composition may be a food composition for alleviation, suppression, or palliation of an inflammatory disease.

In the present disclosure, the food composition may include ingredients commonly added during food production, for example, proteins, carbohydrates, fats, nutrients, seasonings, and flavoring agents, but with no limitations thereto.

In the present disclosure, examples of the carbohydrates include monosaccharides such as glucose and fructose, disaccharides such as maltose, sucrose, and oligosaccharides, polysaccharides such as dextrin and cyclodextrin, and sugar alcohols such as xylitol, sorbitol, and erythritol, but are not limited thereto.

Examples of the flavoring agent according to the present disclosure include, but are not limited to, natural flavoring agents such as thaumatin and *stevia* extract, and synthetic flavoring agents such as saccharin and aspartame.

Advantageous Effects

According to the production method of the present disclosure, extracellular vesicles having wound healing and immunomodulatory effects can be obtained at high yield with high purity by culturing mesenchymal stem cells in an orbital shaking mode in a medium composition containing a noxa protein-derived peptide (peptide), glucose, sucrose, and 3-(N-morpholino)propanesulfonic acid [MOPS].

In addition, the extracellular vesicles derived from mesenchymal stem cells pretreated with a medium composition containing a noxa protein-derived peptide, glucose, sucrose and MOPS of the present disclosure exhibit excellent wound palliation, suppression, or healing effect.

Furthermore, the extracellular vesicles derived from mesenchymal stem cells pretreated with a medium composition containing a noxa protein-derived peptide, glucose, sucrose and MOPS of the present disclosure exhibit an excellent alleviative, suppressive, or therapeutic effect on inflammatory diseases.

BRIEF DESCRIPTION OF THE DRAWINGS

FIG. 1 shows plots of cell viability against the eMTD peptide in terms of absorbance so as to analyze the production of extracellular vesicles, and photographic images of stem cells.

FIG. 2 shows plots of cell viability against the eMTD peptide in terms of cell counts so as to analyze the production of extracellular vesicles, and photographic images of stem cells.

FIG. 3 is a graph of numbers of extracellular vesicles produced per single stem cell after extracellular vesicles are produced and isolated according to an embodiment of the present disclosure.

FIG. 4*a* depicts DLS/NTA graphs showing the average size of Control-EV and the number of particles according to sizes.

FIG. 4*b* depicts DLS/NTA graphs showing the average size of TS-eEV and the number of particles according to sizes.

FIG. 5*a* shows transmission electron microscopic (TEM) images of Control-EV (scale bar: 200 nm).

FIG. 5*b* shows transmission electron microscopic (TEM) images of TS-eEV (scale bar: 200 nm).

FIG. 6 is a graph showing purities of Control-EV and TS-eEV prepared according to an experimental example of the present disclosure.

FIG. 7*a* shows flow cytometry diagrams analyzing whether Control-EV expresses the surface marker CD9-BV421, CD63-PE, or CD81-APC.

FIG. 7*b* shows flow cytometric diagrams analyzing whether TS-eEV expresses the surface marker CD9-BV421, CD63-PE, or CD81-APC.

FIG. 8 shows an image of Western blots analyzing whether the extracellular vesicles of the present disclosure express the antigenic epitopes CD9, CD63, Hsp70, Flotillin-1, Alix, GM130, and β-actin.

FIG. 9 shows confocal microscopic images of stained extracellular vesicles to determine whether the uptake of extracellular vesicles of the present disclosure by HaCaT cells occurs or not.

FIG. 10 is a graph of the cell viability of HaCaT cells in the presence of extracellular vesicles according to the present disclosure.

FIGS. 11*a* and 11*b* are photographic images (11a) and a graph (11*b*) showing the effects of the extracellular vesicles according to the present disclosure on cell migration and proliferation.

FIGS. 12*a* to 12*f* are graphs of levels of nitric oxide and inflammation mediators (iNOS, TNF-α, IL-1β, IL-6, and COX-2) to determine anti-inflammatory effects of the extracellular vesicles according to the present disclosure.

FIG. 13 shows photographic images (a) of a wound site to monitor the wound healing ability of the extracellular vesicles according to the present disclosure and a graph (b) explaining reduction rates of the wound area.

FIG. 14 shows graphs explaining the effect of the action of calcium ions or the calpain enzyme on the production of TS-eEV according to an embodiment of the present disclosure in the process of producing extracellular vesicles of the present disclosure.

BEST MODE FOR CARRYING OUT THE INVENTION

A method for production of mesenchymal stem cell-derived extracellular vesicles, the method including:

a first culturing step of pre-culturing mesenchymal stem cells; and a second culturing step of culturing the pre-cultured mesenchymal stem cells in a medium composition containing a peptide composed of the amino acid sequence of SEQ ID NO: 1, glucose, sucrose, and 3-(N-morpholino)propanesulfonic acid [MOPS].

MODE FOR CARRYING OUT THE INVENTION

A better understanding of the present disclosure may be obtained through the following examples which are set forth to illustrate, but are not to be construed as limiting the present disclosure.

Preparation Example 1. Viability Test Against eMTD Peptide for Preparation of Extracellular Vesicle Mesenchymal stem cells derived from the umbilical cord (Wharton's jelly-derived MSCs, WJ-MSCs) were assayed for viability by treatment with the eMTD peptide at predetermined concentrations for predetermined periods of time.

1-1. Absorbance Analysis

Tests were conducted with predetermined concentrations of the eMTD peptide. In this regard, umbilical cord-derived mesenchymal stem cells were seeded at a density of $2\times10^4$ cells/well into 24-well plates (30024, SPL). After 24 hours of incubation, the eMTD peptide in a sucrose buffer was applied at a final concentration of 0, 0.5, 1, 3, 5, 10, or 20 μM to the cells.

The sequence of the eMTD peptide is given in Table 1.

TABLE 1

| SEQ ID NO: | Name | Sequence listing | Note |
|---|---|---|---|
| 1 | eMTD | KLNFRQKLLNLISKLFCSGT | 20 aa |

The sucrose buffer contained glucose, sucrose, and 3-(N-morpholino)propanesulfonic acid [MOPS] at the respective concentrations shown in Table 2.

TABLE 2

| (mM) | Glucose | Sucrose | MOPS |
|---|---|---|---|
| Sucrose buffer | 5 | 250 | 10 |

After 15 minutes, the cells were incubated with ez-cytox (EZ-3000, DOGEN) for 30 to 60 minutes. Then, absorbance was read at 450 nm using a Bio-RAD x-Mark™ spectrophotometer (Bio-Rad Laboratories, USA).

In addition, treatment with the eMTD peptide was conducted over various times. In this regard, umbilical cord-derived mesenchymal stem cells were seeded at a density of 2×10 4 cells/well into 24-well plates and incubated for 24 hours. Thereafter, the cells were treated with 1 μM of the eMTD peptide in the sucrose buffer for various periods of time (0, 5, 10, 15, 20, 25, or 30 minutes).

After 15 minutes of treatment, the cells were incubated for 30 to 60 minutes with ez-cytox (EZ-3000, DOGEN). Absorbance was read at 450 nm using the Bio-RAD x-Mark™ spectrophotometer (Bio-Rad Laboratories, USA). The results are depicted in FIG. 1 and summarized in Tables 3 and 4.

TABLE 3

| | Ex. 1 | C. Ex. 1 | C. Ex. 2 | C. Ex. 3 | C. Ex. 4 | C. Ex. 5 | C. Ex. 6 |
|---|---|---|---|---|---|---|---|
| MTT assay Concentration (μM) | 1.0 | 0 | 0.5 | 3.0 | 5.0 | 10.0 | 20.0 |
| Cell viability (%) | 57.4 ± 2.48 | 100 ± 0.72 | 53.9 ± 0.72 | 13.6 ± 1.43 | 5.8 ± 1.43 | 2.9 ± 2.48 | 4.1 ± 1.24 |

TABLE 4

| | Ex. 2 | C. Ex. 7 | C. Ex. 8 | C. Ex. 9 | C. Ex. 10 | C. Ex. 11 | C. Ex. 12 |
|---|---|---|---|---|---|---|---|
| MTT assay Time (min) | 15 | 0 | 5 | 10 | 20 | 25 | 30 |
| Cell viability (%) | 37.0 ± 4.28 | 100 ± 1.19 | 52.7 ± 3.14 | 41.8 ± 2.05 | 29.4 ± 3.56 | 18.5 ± 2.38 | 17.8 ± 1.19 |

1-2. Cell Counting

To measure the number of cells, umbilical cord-derived mesenchymal stem cells were seeded at a density of $2.5\times10^4$ cells/well into 12-well plates (30012, SPL) and incubated for 24 hours. The eMTD peptide in the sucrose buffer of Table 2 was applied at a final concentration of 0, 0.5, 1.0, 3.0, 5.0, 10.0, or 20.0 μM to the cells. After 15 minutes, the cells were counted using a trypan blue solution.

Separately, umbilical cord-derived mesenchymal stem cells were seeded at a density of $2.5\times10^4$ cells/well into 12-well plates (30012, SPL) and incubated for 24 hours. The cells were treated with the eMTD peptide in the sucrose buffer of Table 2 for various periods of time (0, 5, 10, 15, 20, 25, and 30 minutes). After each period, the cells were counted using a trypan blue solution, and the results are depicted in FIG. 2 and summarized in Tables 5 and 6.

TABLE 5

| | Ex. 3 | C. Ex. 13 | C. Ex. 14 | C. Ex. 15 | C. Ex. 16 | C. Ex. 17 | C. Ex. 18 |
|---|---|---|---|---|---|---|---|
| TB assay Concentration (μM) | 1.0 | 0 | 0.5 | 3.0 | 5.0 | 10.0 | 20.0 |
| Cell viability (%) | 66.3 ± 10.22 | 100 | 66.7 ± 5.77 | 21.9 ± 4.21 | 11.2 ± 5.30 | 0 | 2.1 ± 3.03 |

TABLE 6

| | Ex. 4 | C. Ex. 19 | C. Ex. 20 | C. Ex. 21 | C. Ex. 22 | C. Ex. 23 | C. Ex. 24 |
|---|---|---|---|---|---|---|---|
| TB assay Time (min) | 15 | 0 | 5 | 10 | 20 | 25 | 30 |
| Cell viability (%) | 38.5 ± 4.71 | 100 | 40.0 ± 0.78 | 29.7 ± 0.78 | 35.9 ± 4.88 | 14.6 ± 1.80 | 15.6 ± 2.34 |

Referring to data in FIGS. 1 and 2 and Tables 3 to 6, selection was made of 1.0 μM for the eMTD peptide concentration and 15 minutes for treatment time, which were experimental conditions accounting for a cell viability of about 50% in order to prepare extracellular vesicles.

Preparation Example 2. EV Isolation and Comparison of Production Output 2-1. Preparation of Control-EV Umbilical cord-derived mesenchymal stem cells were seeded into 150-mm dishes (20151, SPL) (5000 cells/cm 2). When the cells were grown to 80 to 90% confluence, the medium was changed with a-MEM (a-Minimum Essential Medium) (12561072, Gibco) supplemented with 10% exosome-depleted FBS (PS-FB1, PEAK).

After 48 hours of incubation, the a-MEM medium of the culture was obtained. Cell debris was removed by briefly spinning at 300 g for 3 minutes, followed by centrifugation at 2,000 g for 10 minutes. The supernatant was transferred to a new tube which was then again centrifuged at 10,000 g for 30 minutes. The resulting supernatant was again subjected to centrifugation at 187,000 g for 2 hours to obtain Control-EV as a pellet.

2-2. Preparation of eEV (eMTD-EV)

The pellet obtained according to Experimental Example 2-1 was incubated for 15 minutes with the eMTD peptide (1 μM) in the sucrose buffer, followed by isolating eEV (eMTD-EV).

2-3. Preparation of S-eEV (Shaking-eMTD-EV)

The pellet obtained according to Experimental Example 2-1 was incubated for 15 minutes with the eMTD peptide (1 μM) in the sucrose buffer using an orbital shaker (60 RPM) (69455, INFORS HT Celltron), followed by isolating S-eEV (shaking-eMTD-EV).

2-4. Preparation of T-eEV (Trypsinization-eMTD-EV)

When reaching 80 to 90% confluence according to the procedure of Experimental Example 2-1, the cells were floated using trypsin (25200-056, Gibco). Centrifugation of the cell suspension gave a cell pellet which was then incubated for 15 minutes with the eMTD peptide (1 μM) in the sucrose buffer in a 50-ml conical tube (50050, SPL), followed by isolating T-eEV (Trypsinization-eMTD-EV).

2-5. Preparation of TS-eEV (Trypsinization Shaking-eMTD-EV)

The cells were floated according to the procedure of Experimental Example 2-4 and then centrifuged. The cell pellet thus obtained was treated with the eMTD peptide (1 μM) in the sucrose buffer in a 50-ml conical tube (50050, SPL).

The treatment was continued for 15 minutes using an orbital shaker (60 RPM) before isolation of TS-eEV (Trypsinization shaking-eMTD-EV).

2-5. EV Isolation and Comparison of Production Output

The umbilical cord-derived mesenchymal stem cells from which Control-EV, eEV, S-eEV, T-eEV, and TS-eEV have been isolated are summarized for starting cell counts and harvested cell counts, together with incubation times needed to obtain extracellular vesicles, in Table 7.

TABLE 7

| | Starting cell count | Harvested cell count | Incubation time |
|---|---|---|---|
| Control-EV | 5000 cells/$cm^2$ | $10^7$ cells | 2,880 min (48 hr) |
| eEV | 5000 cells/$cm^2$ | $10^7$ cells | 15 min |
| S-eEV | 5000 cells/$cm^2$ | $10^7$ cells | 15 min |
| T-eEV | 5000 cells/$cm^2$ | $10^7$ cells | 15 min |
| TS-eEV | 5000 cells/$cm^2$ | $10^7$ cells | 15 min |

The resulting Control-EV, eEV, S-eEV, T-eEV, and TS-eEV were counted as shown in FIG. 3 and Table 8.

TABLE 8

| | EV production (Particles No./cell) | EV production (Particles No./min) | Total Particles No. |
|---|---|---|---|
| Control-EV | $8.84 \times 10^2 \pm 2.66 \times 10^2$ | $5.45 \times 10^{-1} \pm 2.99 \times 10^{-1}$ | $1.19 \times 10^{10} \pm 9.25 \times 10^9$ |
| eEV | $2.70 \times 10^3 \pm 1.09 \times 10^2$ | $1.80 \times 10^2 \pm 7.25$ | $2.60 \times 10^{10} \pm 1.40 \times 10^9$ |
| S-eEV | $5.32 \times 10^3 \pm 1.17 \times 10^3$ | $3.55 \times 10^2 \pm 7.77 \times 10$ | $4.89 \times 10^{10} \pm 2.14 \times 10^9$ |
| T-eEV | $7.30 \times 10^3 \pm 1.74 \times 10^2$ | $4.86 \times 10^2 \pm 2.00 \times 10$ | $7.30 \times 10^{10} \pm 1.74 \times 10^9$ |
| TS-eEV | $2.39 \times 10^4 \pm 3.42 \times 10^2$ | $1.59 \times 10^3 \pm 2.28 \times 10$ | $2.64 \times 10^{11} \pm 3.78 \times 10^9$ |

As can be seen in FIG. 3 and Table 8, Control-EV was measured to a total particle number of $1.19\times10^{10}\pm9.25\times10^9$, which was increased by about +118.5%, compared to the particle number of $2.60\times10^{10}\pm1.4\times10^9$ for eEV.

S-eEV was counted $4.89\times10^{10}\pm2.14\times10^9$, with about +310.9% improvement compared to Control-EV, T-eEV and TS-eEV were counted $7.30\times10^{10}\pm1.74\times10^9$ and $2.64\times10^{11}\pm3.78\times10^9$, which were improved by about +513.4% and about +2,118.5%, compared to Control-EV, respectively.

Specially, costs for acquiring $1\times10^{10}$ EVs are given in Table 9. TS-eEV was calculated to be about 70 times cheaper than Control-EV.

| | Cost for $1 \times 10^{10}$ particles of EV (₩, won) |
|---|---|
| Control-EV | 49,445 ± 8,024 |
| eEV | 15,515 ± 1,032 |
| S-eEV | 4,114 ± 307 |
| TS-eEV | 721 ± 20 |

Experimental Example 1. EV Characterization 1-1. Analysis for EV Size and Particle Number by EV Size The size of EVs was measured by dynamic light scattering (DLS) analysis using a Nano Zetasizer (Malvern Instruments, Melbourne, UK). EVs were measured for size and counted using a nanoparticle tracking analyzer (NTA) NS300 (Nanosight, Amesbery, UK). The results are depicted in FIGS. 4*a* and 4*b*.

As shown in FIGS. 4*a* and 4*b*, the average size was measured to be 159 nm for Control-EV and 90 nm for TS-eEV.

1-2. Morphological Analysis for EV

EVs were morphologically analyzed using a transmission electron microscope (TEM, JEM-1010, Nippon Denshi, Tokyo, Japan) at 80 kV, and the results are given in FIGS. 5*a* and 5*b* (Scale bar: 200 nm).

As shown in FIGS. 5*a* and 5*b*, Control-EV and TS-eEV were morphologically similar.

1-3. Analysis for EV Purity

Particle numbers were determined using NTA. Further, proteins were quantitated using a BCA kit, followed by measuring purity of EV (particles/ug protein). The results are given in FIG. 6 and Table 10.

TABLE 10

| | Particles/ug protein |
|---|---|
| Control-EV | $3.22 \times 10^8 \pm 1.22 \times 10^8$ |
| TS-eEV | $1.61 \times 10^{10} \pm 5.86 \times 10^9$ |

As shown in FIG. 6 and Table 10, TS-eEV was counted $1.61\times10^{10}\pm5.86\times10^9$, with about +4,900% purity improvement, compared to Control-EV counted $3.22\times10^8\pm1.22\times10^8$.

Control-EV was obtained by culturing cells and thus was highly likely to be in mixture with various substances secreted from cells, such as soluble proteins or cytokines.

1-4. Identification of Surface Marker on EV

The EVs were captured using Exosome-Human CD9 Flow Detection Reagent (Invitrogen, 10620D), and dyed with CD9-BV421 (743047, BD), CD63-PE (556020, BD), or CD81-APC (130-119-787, Miltenyi Biotec), followed by flow cytometry (Beckman Coulter/CytoFLEX). The results are depicted in FIGS. 7*a* and 7*b*.

As shown in FIG. 7*a*, Control-EV expressed CD9, CD63, and CD81 as surface markers. In FIG. 7*b*, CD9, CD63, and CD81 were detected as surface markers on TS-eEV.

Umbilical cord-mesenchymal stem cells were lysed with a RIPA buffer (CBR002, LPS solution) containing a protease inhibitor cocktail (87786, Invitrogen) to give a whole cell lysate (WCL). WCL and EV were run in 4-12% Bis-Tris Flus Gels (NW04125BOX, Invitrogen/NW04122BOX, Invitrogen) by electrophoresis and then transferred onto an NC membrane (IB23001, Invitrogen). The NC membrane was incubated overnight at 4° C. with a primary antibody (1:1000) and washed three times with 1×TBST (TLP-118.1, Translab). Subsequently, the membrane was reacted at room temperature for 2 hours with a secondary antibody before being washing with 1×TBST.

The primary and secondary antibodies were as follows: anti-CD9 antibody (ab263023, Abcam), anti-CD63 antibody (ab134045, Abcam), anti-HSP70 antibody (4876, CST), anti-Flotillin-1 antibody (18634, CST), anti-Alix antibody (2171, CST), anti-GM130 antibody (12480, CST), β-actin antibody (sc-47778, Santa Cruz), HRP linked anti-rabbit IgG (7074, CST), and HRP linked anti-mouse IgG (7076, CST).

All the antibodies were diluted in 1× blocking buffer (TLP-115.1G, Translab) before use, and images were taken using Invitrogen™ iBright™ Imagers (CL-1000). The results are depicted in FIG. 8.

As can be seen in FIG. 8, the exosome-positive markers CD9, CD63, Hsp70, Flotillin-1, and Alix were expressed whereas the exosome-negative marker GM130 (Golgi body marker) was not expressed.

1-5. EV Uptake of HaCaT Cells

EVs were dyed with 2 μg/ml DiR (D12731, Invitrogen) at room temperature for one hour. Thereafter, free dye was removed using an ultracentrifuge at 178,000×g for two hours. HaCaT cells were incubated with $3\times10^9$ EVs for six hours and then stained with DAPI (4', 6-diamidino-2-phenylindole) [VECTASHIELD® Antifade Mounting Medium with DAPI-(H-1200)] and CellMask™ (Green Plasma Membrane Stain, C37608, Invitrogen). The stained HaCaT cells were observed by confocal laser microscopy (Carl Zeiss LSM 800), and the results are depicted in FIG. 9.

As shown in FIG. 9, TS-eEV was uptaken by HaCaT cells.

Experimental Example 2. Assay for Wound Healing and Anti-Inflammation Effect

2-1. Viability Test

HaCaT cells were tested for viability against Control-EV and TS-eEV. In this regard, HaCaT cells were seeded at a density of $1\times10^4$ cells/well into 96-well plates (30096, SPL). After 24 hours of incubation, the medium was changed with DMEM-high glucose (D6046, Sigma) supplemented with 10% exosome-depleted FBS and treated for 24 hours with predetermined numbers of EVs ($1\times10^6$, $1\times10^7$, $1\times10^8$, or $1\times10^9$ particles). After 24 hours, the cells were incubated for one hour with ez-cytox (EZ-3000, DOGEN). Absorbance was read at 450 nm using Bio-RAD x-Mark™ spectrophotometer (Bio-Rad Laboratories, USA). The results are depicted in FIG. 10 and summarized in Table 11

TABLE 11

| | Cell viability (%) | | | | |
|---|---|---|---|---|---|
| EV particles | Control | $1 \times 10^6$ | $1 \times 10^7$ | $1 \times 10^8$ | $1 \times 10^9$ |
| Control-EV | 100 | 103.4 ± 0.86 | 105.8 ± 0.46 | 109.1 ± 1.12 | 121.6 ± 22.66 |
| TS-eEV | 100 | 106.0 ± 0.37 | 106.8 ± 4.46 | 110.8 ± 6.90 | 120.0 ± 0.74 |

As understood from the data of FIG. 10 and Table 11, TS-eEV increased the cell viability in a dose-dependent manner, with the relative increase of cell viability by about +20% upon treatment with $1\times10^9$ particles to the control. There was no significant difference in cell viability between Control-EV and TS-eEV groups.

2-2. Cell Migration and Proliferation Effect

In order to examine the effects of Control-EV and TS-eEV on cell migration and proliferation, HaCaT cells were seeded at a density of $6\times10^5$ cells/well into 6-well plates (32006, SPL) and grown to 95% confluency, followed by incubation with 10 μg/ml mitomycin C (M4287, Sigma) for two hours to inhibit cell proliferation.

The cells were scratched using a 1-ml pipette tip and treated with Control-EV or TS-eEV ($1\times10^9$ particles/ml) for 24, 48, or 72 hours. The effects of Control-EV and TS-eEV on cell migration and proliferation were observed under a microscope. The resulting images are given in FIG. 11*a* while relative wound areas are depicted in FIG. 11*b* and summarized in Table 12. The control culture (PBS) was not treated with EVs, but with PBS.

In Table 12, relative wound areas for Con-EV and TS-eEV over time are numerically expressed, with normalization to the value 100 set for the control of FIG. 11*b*.

TABLE 12

| Wound area (%) | Control | 24 h | 48 h | 72 h |
|---|---|---|---|---|
| Control (PBS) | 100 | 86.3 ± 2.05 | 65.5 ± 2.05 | 30.0 ± 1.28 |
| Control-EV | 100 | 74.8 ± 2.37 | 44.5 ± 5.19 | 10.4 ± 9.98 |
| TS-eEV | 100 | 75.5 ± 4.06 | 44.2 ± 8.49 | 10.7 ± 5.08 |

As can be seen in FIGS. 11*a* and 11*b* and Table 12, TS-eEV decreased the wound area from 100 to 10.7±5.08 while the control (PBS) decreased from 100 to 30.0±1.28. That is, TS-eEV increased cell migration by about +19.3%, compared to the control (PBS).

There was no significant difference between Control-EV and TS-eEV, and treatment with $1\times10^9$ particles of TS-eEV increased cell migration by about +27.0% or more, compared to the control (PBS).

2-3. Anti-Inflammatory Effect

Raw264.7 cells were seeded at a density of $1.5\times10^5$ cells into 24-well plates and incubated for 12 hours. Then, $1\times10^8$ or $1\times10^9$ particles of Control-EV was applied, together with 10 ng/ml LPS (L4391-1MG, Sigma), to 300 μl of the Raw264.7 cell culture. In addition, $1\times10^8$ or $1\times10^9$ particles of TS-eEV, instead of Control-EV, were applied to 300 μl of the Raw264.7 cell culture.

After 18 hours of incubation, the culture supernatant was obtained and reacted with the Griess reagent [0.1% N-(1-naphthyl) ethylenediamide dihydrochloride and 1% sulfanilamide in 5% phosphoric acid], followed by reading absorbance at 540 nm to quantitatively analyze nitric oxide (NO). The results are depicted in FIG. 12*a* and summarized in Table 13. Separately, mRNA was extracted, and analyzed for relative expression levels of iNOS, TNF-alpha, IL-1beta, IL-6, and COX2 by real-time PCR. The results are depicted in FIGS. 12*b* to 12*f* and summarized in Table 13.

TABLE 13

| | Control | LPS only | Con-EV ($1 \times 10^8$) | Con-EV ($1 \times 10^9$) | TS-eEV ($1 \times 10^8$) | TS-eEV ($1 \times 10^9$) |
|---|---|---|---|---|---|---|
| NO (μM) | 1.0 ± 0.21 | 21.7 ± 0.4 | 16.9 ± 2.89 | 15.1 ± 1.44 | 17.9 ± 0.2 | 15.0 ± 0.20 |
| miNOS | 1.0 ± 0.13 | 2.69 ± 0.27 | 1.74 ± 0.18 | 1.47 ± 0.14 | 1.69 ± 0.23 | 1.46 ± 0.08 |
| mTNF-α | 1.0 ± 0.09 | 2.28 ± 0.57 | 1.78 ± 0.29 | 1.46 ± 0.28 | 1.68 ± 0.33 | 1.46 ± 0.07 |
| mIL-1β | 1.0 ± 0.06 | 4.18 ± 0.52 | 2.28 ± 0.59 | 1.89 ± 0.14 | 2.7 ± 0.33 | 1.51 ± 0.13 |
| mIL-6 | 1.0 ± 0.08 | 1.62 ± 0.1 | 0.85 ± 0.15 | 0.74 ± 0.15 | 0.97 ± 0.09 | 0.71 ± 0.04 |
| mCOX2 | 1.0 ± 0.07 | 2.87 ± 0.67 | 1.32 ± 0.38 | 1.29 ± 0.13 | 1.77 ± 0.32 | 1.56 ± 0.22 |

As can be seen in FIGS. 12*a* to 12*f* and Table 13, the nitric oxide (NO) level was measured to be 17.9±0.2 μM upon treatment with $1\times10^8$ particles of TS-eEV and thus decreased by about −17.5%, compared to 21.7±0.4 μM measured for LPS only.

The NO level was measured to be 15.0±0.20 μM upon treatment with $1\times10^9$ particles of TS-eEV and thus decreased by about −45.8%, compared to 21.7±0.4 μM measured for LPS only.

The expression level of iNOS, an inflammation mediator, was measured to be 1.46±0.08 and thus decreased by about −45.7%, compared to 2.69±0.27 measured for LPS only.

The expression level of TNF-α was measured to be 1.46±0.07 and thus decreased by about −36.0%, compared to 2.28±0.57 measured for LPS only.

The expression level of IL-113 was measured to be 1.51±0.13 and thus decreased by about −63.9%, compared to 4.18±0.52 measured for LPS only.

The expression level of IL-6 was measured to be 0.71±0.04 and thus decreased by about −56.2%, compared to 1.62±0.1 measured for LPS only.

The expression level of COX2 was measured to be 1.56±0.22 and thus decreased by about −45.6%, compared to 2.87measured for LPS only.

As understood from the data, the LPS (Lipopolysaccharide)-induced inflammatory response in Raw 264.7 (mouse macrophage) cells can be reduced by TS-eEV, which demonstrates the anti-inflammatory effect of TS-eEV.

Experimental Example 3. In Vivo Wound Healing Assay

BALB/c nude female mice at 6 weeks of age were purchased and acclimated for one week. After a tissue wound was induced using a 5-mm biopsy punch (Kai, BP-50F), Control-EV or TS-eEV was applied at a concentration of $1\times10^9$ particles/20 μl to the wound site that was monitored every day by photography to determine wound areas. The results are depicted in FIG. 13 and summarized in Table 14.

TABLE 14

| Relative Wound area (%) | Day 0 | Day 2 | Day 3 | Day 5 | Day 7 |
|---|---|---|---|---|---|
| Control (PBS) | 100 | 71.2 ± 11.40 | 59.6 ± 11.06 | 50.5 ± 7.89 | 29.5 ± 4.62 |
| Control-EV | 100 | 63.3 ± 27.42 | 46.6 ± 18.16 | 38.0 ± 14.85 | 18.3 ± 10.22 |
| TS-Eev | 100 | 59.1 ± 15.02 | 37.6 ± 15.30 | 29 ± 16.71 | 15.4 ± 4.05 |

As can be seen in FIG. 13 and Table 14, there was no significant difference between Control-EV and TS-eEV groups. TS-eEV was detected to leave a relative wound area of 15.4% and further reduce the relative wound area by about −48.0%, compared to the control (PBS), showing improved wound healing ability. In addition, TS-eEV further reduced the relative wound by about −15.8%, compared to 18.3% measured for Control-EV, exhibiting an improvement in would healing ability, compared to Control-EV.

Experimental Example 4. Inhibitor Assay

The cells were pretreated with 50 μM BAPTA-AM (calcium-selective chelator) for 1 hour and with 10 μM ALLM (calpain inhibitor) for 18 hours. Comparison was made of EV production outputs among the method used, and the results are shown in FIGS. 14*a* and 14*b* and Table 15.

TABLE 15

| | EV production (particle number/cell) | EV production (particle number/min) |
|---|---|---|
| Control-EV | $8.14 \times 10^2 \pm 1.99 \times 10^2$ | $4.98 \times 10^{-1} \pm 2.55 \times 10^{-1}$ |
| eEV | $3.02 \times 10^3 \pm 2.45 \times 10$ | $2.01 \times 10^2 \pm 1.63$ |
| S-eEV | $5.20 \times 10^3 \pm 2.51 \times 10^3$ | $3.47 \times 10^2 \pm 1.67 \times 10$ |
| T-eEV | $6.92 \times 10^3 \pm 3.181 \times 10^2$ | $4.62 \times 10^2 \pm 2.12 \times 10$ |
| TS-eEV | $1.97 \times 10^4 \pm 1.31 \times 10^3$ | $1.31 \times 10^3 \pm 8.77 \times 10$ |
| TS-eEV with BAPTA-AM | $7.34 \times 10^3 \pm 9.08 \times 10^2$ | $4.89 \times 10^2 \pm 6.06 \times 10$ |
| TS-eEV with ALLM | $8.25 \times 10^3 \pm 9.96 \times 10^2$ | $5.50 \times 10^2 \pm 6.64 \times 10$ |

As understood from the data in FIGS. 14*a* and 14*b* and Table 15 showing the results of TS-eEV isolation, the EV production from the groups treated with the inhibitor BAPTA-AM or ALLM was decreased to less than 60% of those from the groups treated without the inhibitor. In the light of the fact that the EV production rate was reduced, the action of calcium ions (BAPTA-AM calcium chelator) and the calpain enzyme (ALLM calpain inhibitor) are thought to play important roles in the production of TS-eEV.

INDUSTRIAL APPLICABILITY

The present disclosure relates to a method for mass production of extracellular vesicles, using a peptide derived from Noxa protein and mesenchymal stem cells and, specifically, a method for mass production of extracellular vesicles, wherein mesenchymal stem cells are cultured in a medium composition containing a Noxa protein-derived peptide, glucose, sucrose, and 3-(N-morpholino)propanesulfonic acid (MOPS), whereby extracellular vesicles having wound healing and immunomodulatory effects can be obtained with high purity at high yield.

The invention claimed is:

1. A method for producing extracellular vesicles derived from Wharton's jelly-derived mesenchymal stem cells (WJ-MSCs), the method comprising:

a first culturing step of pre-culturing (WJ-MSCs); and a second culturing step of culturing the pre-cultured (WJ-MSCs) in a medium composition containing a peptide composed of the amino acid sequence of SEQ ID NO: 1, glucose, sucrose, and 3-(N-morpholino) propanesulfonic acid [MOPS], wherein the peptide composed of the amino acid sequence of SEQ ID NO: 1 is contained at a concentration of 0.1 to 5.0 uM in the medium composition.

2. The method of claim 1, wherein the first culturing step further comprises a trypsin treatment step of treating the pre-cultured mesenchymal stem cells with trypsin.

3. The method of claim 1, wherein the second culturing step is performed in an orbital shaking culture manner.

4. The method of claim 1, wherein the second culturing step is performed for 5 to 30 minutes.

5. The method of claim 1, wherein glucose is contained at a concentration of 1 to 10 mM in the medium composition.

6. The method of claim 1, wherein sucrose is contained at a concentration of 200 to 300 mM.

7. The method of claim 1, wherein MOPS is contained at a concentration of 1 to 20 mM in the medium composition.

8. The method of claim 1, further comprising an isolation step of isolating the mesenchymal stem cell-derived extracellular vesicles.

* * * * *